(12) United States Patent
Mujumdar et al.

(10) Patent No.: US 7,615,646 B2
(45) Date of Patent: Nov. 10, 2009

(54) CHIRAL INDOLE INTERMEDIATES AND THEIR FLUORESCENT CYANINE DYES CONTAINING FUNCTIONAL GROUPS

(75) Inventors: Ratnaker B. Mujumdar, Placentia, CA (US); Richard Martin West, Buckinghamshire (GB)

(73) Assignees: Carnegie Mellon University, Pittsburgh, PA (US); GE Healthcare UK Limited, Buckinghamshire (GB)

( * ) Notice: Subject to any disclaimer, the term of this patent is extended or adjusted under 35 U.S.C. 154(b) by 507 days.

(21) Appl. No.: 10/513,141

(22) PCT Filed: May 9, 2003

(86) PCT No.: PCT/US03/14632

§ 371 (c)(1),
(2), (4) Date: Jan. 28, 2005

(87) PCT Pub. No.: WO2004/039894

PCT Pub. Date: May 13, 2004

(65) Prior Publication Data

US 2006/0051758 A1    Mar. 9, 2006

Related U.S. Application Data

(60) Provisional application No. 60/379,107, filed on May 10, 2002.

(51) Int. Cl.
*C07D 403/06* (2006.01)
*C12Q 1/00* (2006.01)

(52) U.S. Cl. ............... 548/455; 435/4; 435/6; 435/7.2; 548/465; 548/467; 548/484

(58) Field of Classification Search ........ 548/467, 548/484, 465, 455; 435/4, 6, 7.2
See application file for complete search history.

(56) References Cited

U.S. PATENT DOCUMENTS 5,268,486 A    12/1993    Waggoner et al.
6,133,445 A    10/2000    Waggoner et al.
6,180,087 B1    1/2001    Achilefu et al.

FOREIGN PATENT DOCUMENTS

WO    WO 00/75237 A2    12/2000
WO    WO 02/26891    4/2002
WO    WO 02/26891 A1    4/2002

OTHER PUBLICATIONS

Supplementary European Search Report dated Apr. 28, 2005, issued in connection with EP 03 80 8367.
Capper et al, "Assessing a Training Screen Employing Image-based Cellular Assays—Antagonist GPCR assays in live-cells with CypHer5E", Poster presented at the 10th SBS Conference, Orlando, Florida, Sep. 10-15, 2004.
Newman et al, "Detection of Agonist-mediated Internalization of Endogenous EGF Receptors Using CypHer5E", 4th BPS Focused Meeting on Cell Signaling, Leicester, UK Apr. 11-12, 2005.
Beletskii et al, "High-throughput phagocytosis assay utilizing a pH-sensitive fluorescent dye", BioTechniques 39(6):894-897, Dec. 2005.
Screening for potential β2-adrenergic receptor antagonists using CypHer5E and IN Cell Analyzer 1000, in Discovery Matters Issue 3, p. 13, Mar. 2006.
Optimization of CypHer5E labeled anti-VSV-G antibody for use in receptor internalization assays, Discovery Matters Issue 5, p. 17, Mar. 2007.
Handbook of Fluorescent Probes and Research Products, Richard P. Haughland, 9th Edition, Molecular Probes.
Non-Radioactive Labelling: A Practical Introduction, Biological Techniques Series, Andrew J. Garman, Academic Press (1997).
Bioconjugation—Protein Coupling Techniques for the Biomedical Sciences, Mohammed Aslam and Alastair Dent. Macmillan (1998).
Brinkley, "A Brief Survey of Methods for Preparing Protein Conjugates with Dyes, Haptens, and Cross-Linking Reagents", Bioconjugate Chemistry (1992), vol. 3, No. 1, pp. 2-13.
Handbook of Fluorescent Probes and Research Products, Richard P. Haughland, 9th Edition, Molecular Probes (2002).

*Primary Examiner*—Charanjit S Aulakh
(74) *Attorney, Agent, or Firm*—Nixon & Vanderhye P.C.

(57) ABSTRACT

This invention relates to the functionalized cyanine dyes and more particularly, to the synthesis of chiral 3-substituted 2,3'-dymethyl-3H-indole and its derivatives as intermediates for preparation of cyanine dyes, to methods of preparing these dyes and the dyes so prepared.

9 Claims, 9 Drawing Sheets

General scheme for the synthesis of functionalized ketone (A) and its cyanine dyes $^1$H NMR spectra of Cy3.18.OH and NSCy3 in $D_2O$. Some of the methylene protons of the hexanoic acid chain in NSCy3 are shielded by heterocyclic ring and appeare upfield. (shown by arrow).

Absorption spectra of non-sulfonated Cy3 isomers and their antibody conjugates.

Relative fluorescence intensities of Cy3 dyes. Absorption is o.o5 at 550 nm and excitation wavelength in 514 nm. Ncy3 is brighter in PBS solution suggesting less dye/dye aggregation.

NSCy3.18.OH        Cy3.18.OH

Sulfonated Cy3 dicarboxylic acid isomers

CHIRAL INDOLE INTERMEDIATES AND THEIR FLUORESCENT CYANINE DYES CONTAINING FUNCTIONAL GROUPS

This application is the U.S. national phase of international application PCT/US2003/014632, filed 9 May 2003, which claims benefit of U.S. Provisional Application Ser. No. 60/379,107, filed May 10 2002, the entire contents of each of which are incorporated herein by reference.

The U.S. Government has a paid-up license in this invention and the right in limited circumstances to require the patent owner to license others on reasonable terms as provided for by the terms of NIH Grant No. R01-NS-19353 and NSF Grant No. MCB-8920118.

This invention relates to the functionalized cyanine dyes and more particularly, to the synthesis of chiral 3-substituted 2,3'-dimethyl-3H-indole and its derivatives as intermediates for preparation of cyanine dyes, to methods of preparing these dyes and the dyes so prepared.

Highly fluorescent carboxyl containing indocyanines are useful as labeling reagents for biological investigations. Functional groups on the dyes permit covalent binding to biomaterials and/or other non-biological materials for purpose of fluorescence detection, while water soluble arylsulfonate groups reduce dye-dye aggregation and enhance fluorescence brightness (see US patents by Waggoner et. al U.S. Pat. Nos. 5,268,486; 5,486,616; 5,569,587; 5,852,191; 5,981,747; 5,986,093).

The carboxylic and arylsulfonate groups occupy key positions in the heteroaromatic bases such as $R_1$ and $R_2$ in (1), and thereby restrict the ability for dye modifications.

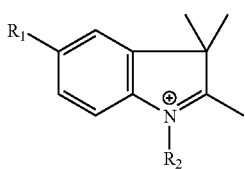

(1)

wherein $R_1$ is $CH_2NH_2$, $CH_2COOH$, $SO_3H$ or H and $R_2$ is $(CH_2)_mNH_2$, $(CH_2)_mCOOH$, $(CH_2)_mSO_3H$ or $(CH_2)_mOH$, and m is an integer ranging from 1 to 6.

Thus, it is of interest to synthesize compounds with functional groups at different sites in the indole bases. These new intermediates will enable chemists to synthesize a wide range of cyanines.

Chiral 2,3-dimethyl-3H indoles (2) are expected to possess exceptional advantages as a precursor of a family of cyanine dyes for use as covalently attached fluorescent labels for biological research. Disclosed herein is a convenient synthesis of various 3-substituted 2-butanones and their conversion to cyanine dyes (FIG. 1). These dyes are very similar to those described in the U.S. Pat. No. 5,268,486 and other related publications of the inventor, such as, for example, listed herein which disclose luminescent mono- and polymethinecyanine and related dyes such as merocyanine and styryl dyes which contain groups enabling these dyes to covalently attach to amine, hydroxyl, aldehyde and sulphydryl groups on a target material. The disclosed compounds fluoresce in the green, orange, red and near infrared regions of the spectrum.

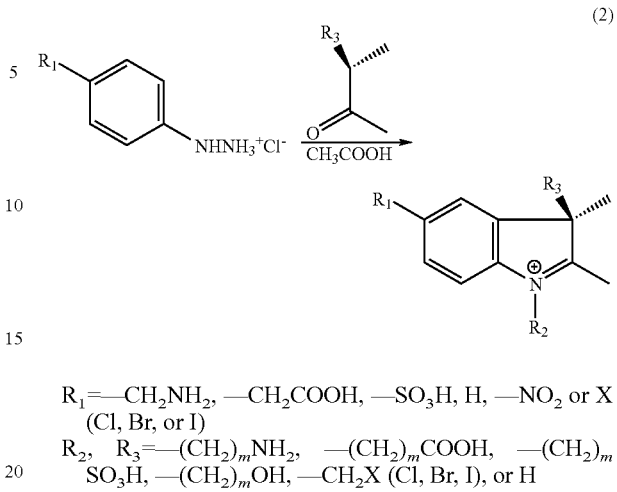

$R_1$=—$CH_2NH_2$, —$CH_2COOH$, —$SO_3H$, H, —$NO_2$ or X (Cl, Br, or I)

$R_2$, $R_3$=—$(CH_2)_mNH_2$, —$(CH_2)_mCOOH$, —$(CH_2)_mSO_3H$, —$(CH_2)_mOH$, —$CH_2X$ (Cl, Br, I), or H wherein m is an integer ranging from 1 to 6.

Rosenstock (Research Laboratories, The National Drug Company, NOTES (December 1966 pp. 537-539) has described the synthesis of a plant growth hormone by means of Fischer indolization of levulinic acid phenylhydrazone. The indole is used for the development of various plant growth hormones.

WO 02/26891 discloses cyanine dyes incorporating similar structures.

A number of papers, such as Eggers et al (Angew. Chem. Int. Ed. Engl. (1997) 36, No. 8, 881-883), Eggers et al (Liebigs Ann. (1996), 979-983), Reichardt et al (Chem. Rev. 123, (1990), 565-581), Reichardt et al (Liebigs Ann. (1995) 329-340), and U.S. Pat. Nos. 6,190,641; 6,183,726; 6,180,087; 6,180,086 and 6,180,085 have described the synthesis of chiral indoles such as (3). Cyanine dyes described in these papers are water insoluble and have no functional groups that react with biological specimens. The chiral indoles are obtained by direct alkylation of 2,3-dimethylindole as shown below. This method has very limited applications. Attempts to alkylate 2,3-dimethylindole with various alkylhalides (such as 6-iodo ethylhexanoate) have been unsuccessful.

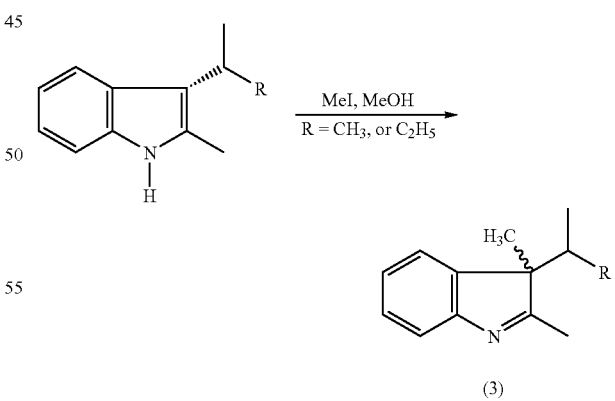

(3)

BRIEF DESCRIPTION OF THE DRAWINGS

The FIGS. 2-9 emphasize improved properties of the cyanine dyes of the present invention due to the modifications at the 3, 3' positions of the indolenine. Specifically, FIG. 2 shows a computer generated, energy minimized structure of 6-(1,2-dimethyl-7-sulfo-3-hydrobenz[e]indolyl)hexanoic acid. The hexanoic acid chain is perpendicular to the plane of benzindole ring. Some of alkyl protons of the hexanoic acid chain are over the plane of the ring. This is also substantiated by the NMR spectrum of 5-(2,3-dimethyl-3H-indol-3-yl)pentan-1-ol (Example 9) and 6-(2,3-dimethyl-3H-indol-3-yl) hexanoic acid (Example 3) in FIG. 3. The alkyl chain protons or hexanoic acid and pentanol are shielded due to indole ring and therefore appear at high field (0.5-0.7 ppm). In FIG. 4, the NMR of NSCy3 shows similar up-field protons (shown by arrow). The hexanoic acid protons for Cy3.18 appear at 1.5-2.0 ppm. Such a configuration prevents dye-dye aggregation thereby increasing the fluorescence brightness of the dye in aqueous solutions. This is a major advantage of these new intermediates of this invention. FIG. 5 shows the absorbance spectra of three non-sulfonated Cy3 dyes and their IgG conjugates. Cy3.10-IgG conjugates (FIG. 5C) show considerable deviation from the base line suggesting significant dye-dye aggregation. The spectrum Cy3.24 and its IgG conjugates (FIG. 5B) and NCy3 and its IgG conjugates (FIG. 5A) are almost identical. But NCy3 is 20-25% brighter than Cy3.24 in aqueous solution. This is shown in FIG. 6. The equal concentration of the dyes in methanol and PBS solutions were excited at 514 nm; fluorescence intensities of the dyes in methanol are almost the equal. Because of high solubility in methanol, no dye-dye aggregation is observed. However, in a phosphate buffer solution, NSCy3 is 20-25% brighter than Cy3.24. The reduction of dye-dye aggregation in an antibody conjugated dyes is also evident from FIG. 7. The absorption spectra of commercialized Cy7.18 and new NSCy7 are compared with their antibody conjugates. Cy7.18 aggregates more on antibody as seen from the increase in the vibronic shoulder.

Figure 1:
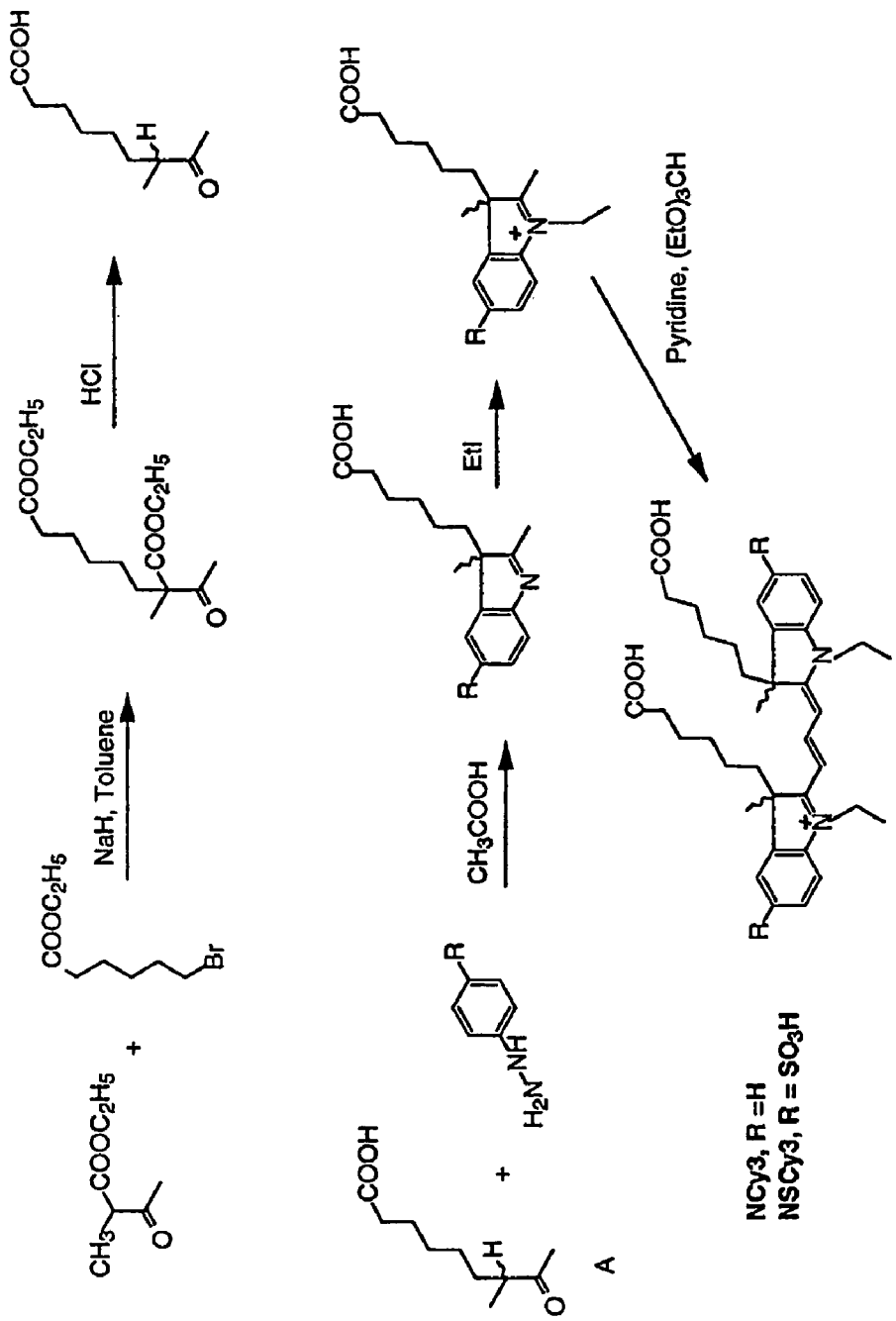
FIG. 1: A General scheme for the synthesis of 3-substituted-2-butanone and its cyanine dyes.
Figure 2:
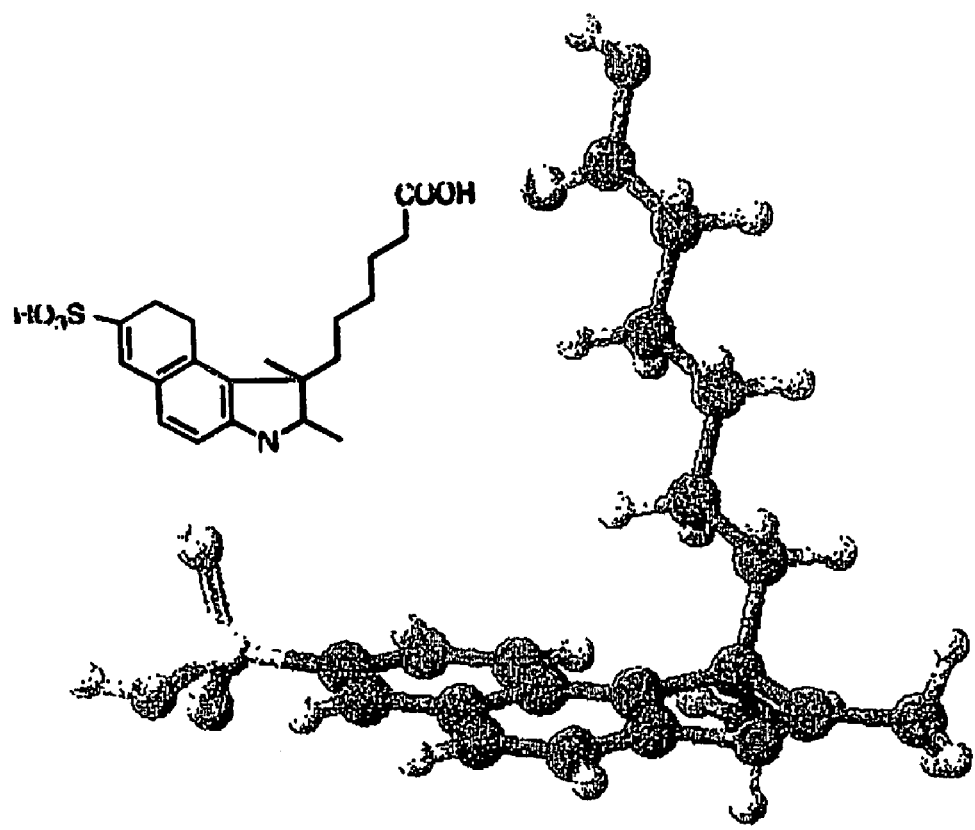
FIG. 2: Computer generated energy minimized structure of 6-(1,2-dimethyl-7-sulfohydrobenzo[e]indolyl)hexanoic acid. The hexanoic acid chain is almost perpendicular to the benzindole ring. Such a configuration of the chain prevents dye-dye aggregation.
Figure 3:
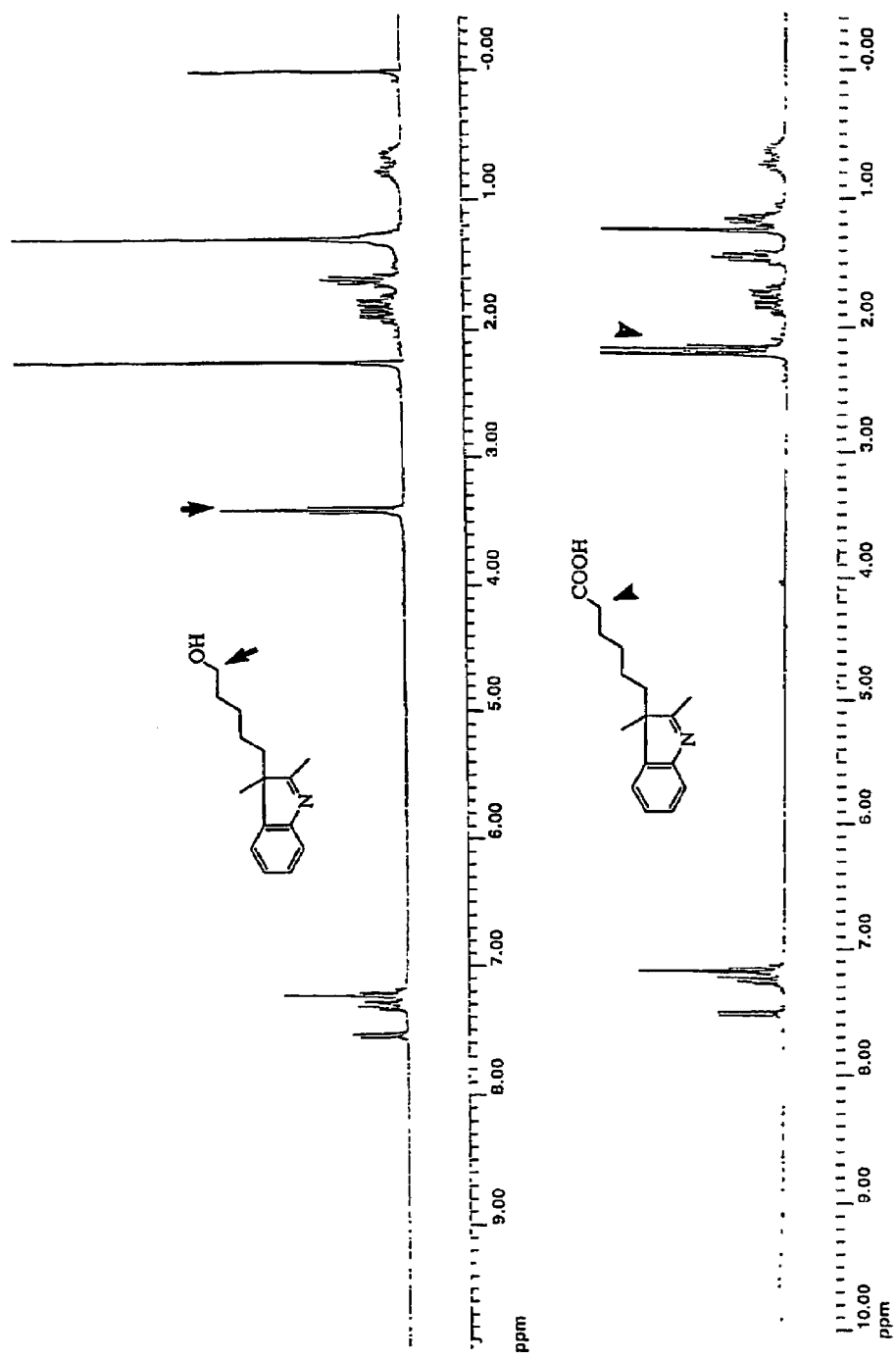
FIG. 3: $^1$H NMR spectra in CDCl$_3$ of 6-(2,3-dimethyl-3H-indol-3-yl)hexanoic acid and 5-(2,3-dimethyl-3H-indol-3-yl)pentan-1-ol show identical aromatic signals. Some of the methylene protons of the hexanoic acid and pentanol alkyl chains show high field shift, suggesting shielding of those protons due to ring current effect of the indole.
Figure 4:
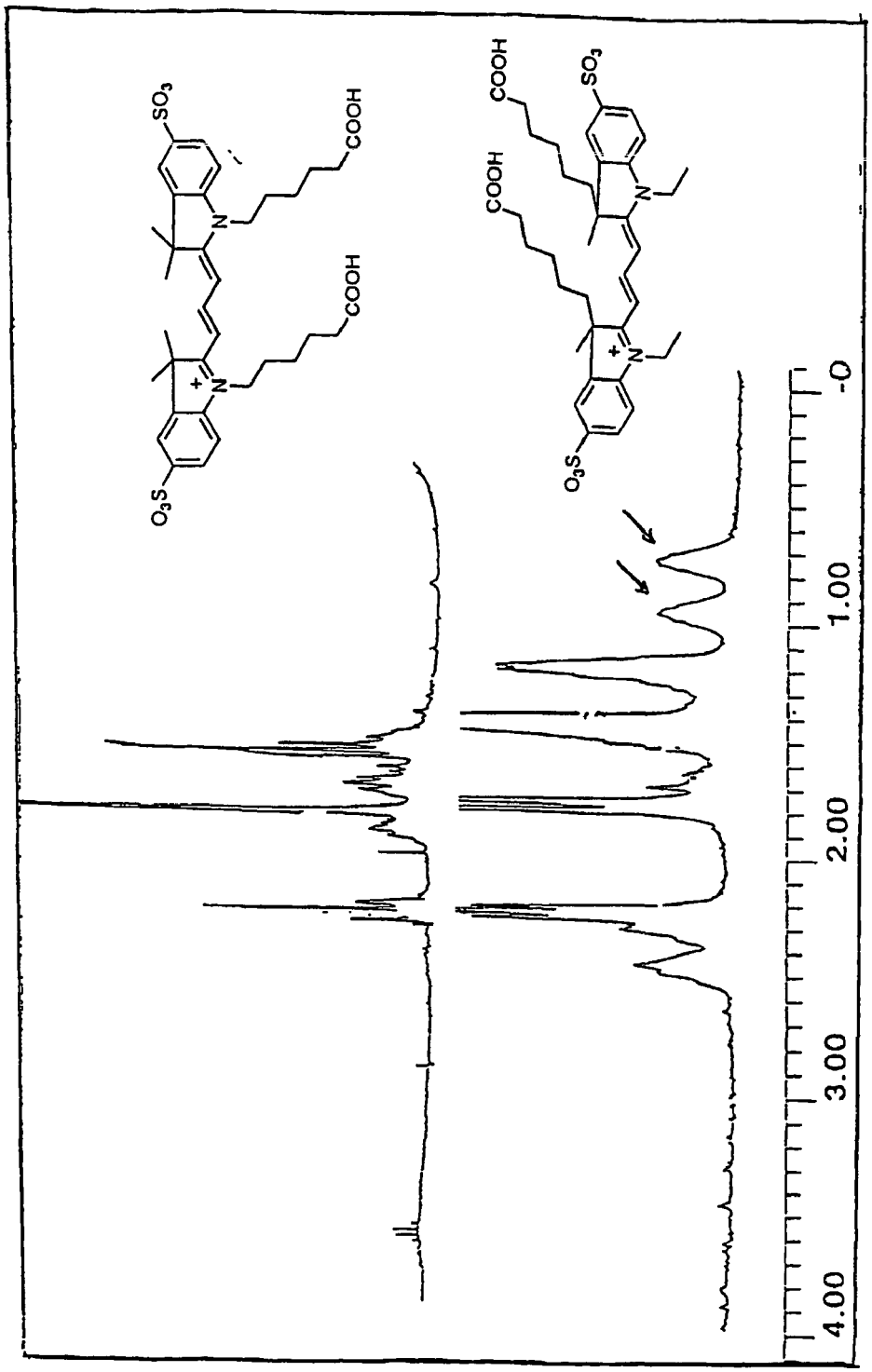
FIG. 4: $^1$H NMR spectra of Cy3.18 and NS Cy3 in D$_2$O. Some of the methylene protons of the hexanoic acid chain in NSCy3 show high field shift, suggesting shielding of those protons due to ring current effect of the indole.
Figure 5:
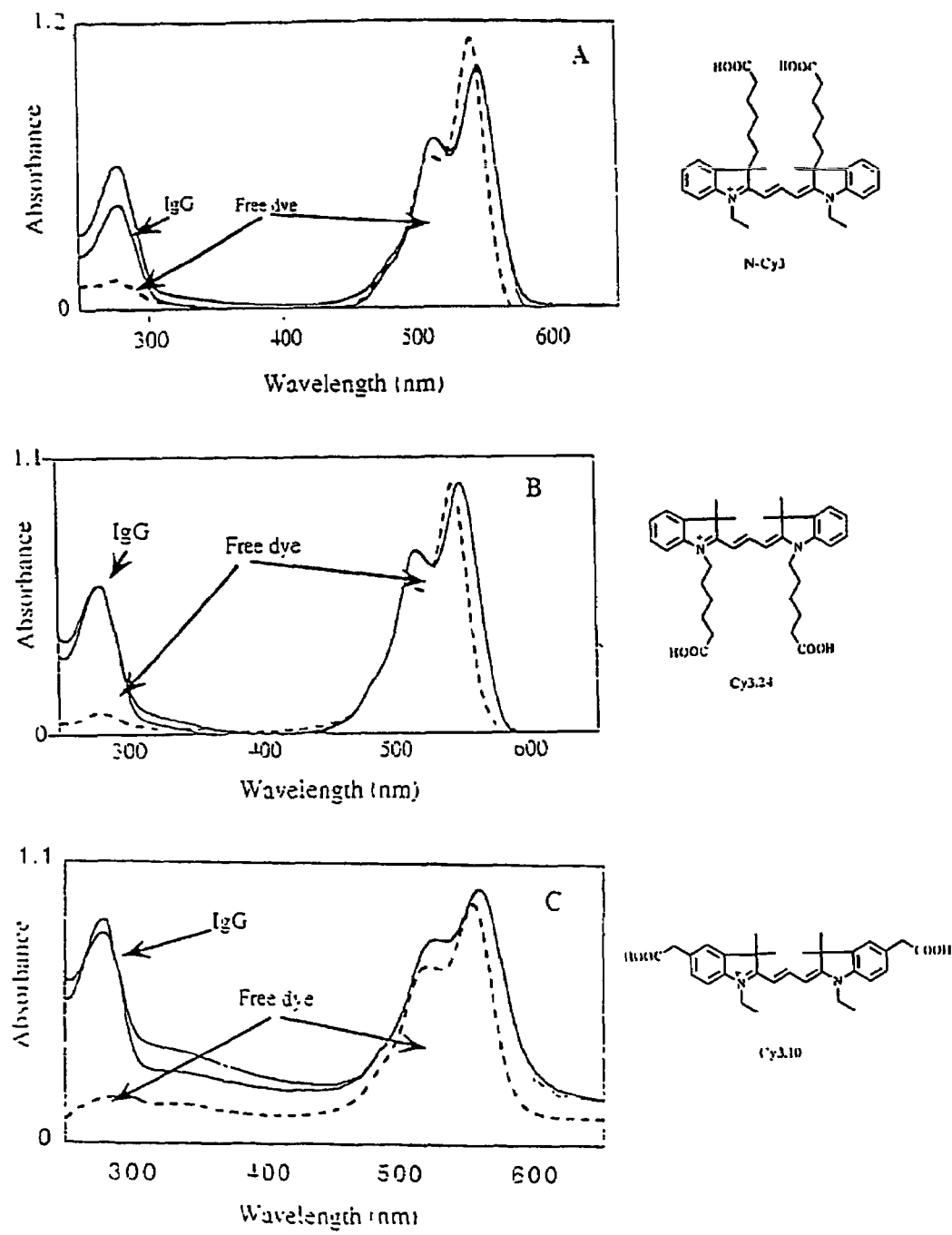
FIG. 5: Absorption spectra of non-sulfonated Cy3 isomers and their antibody conjugates.
Figure 6:
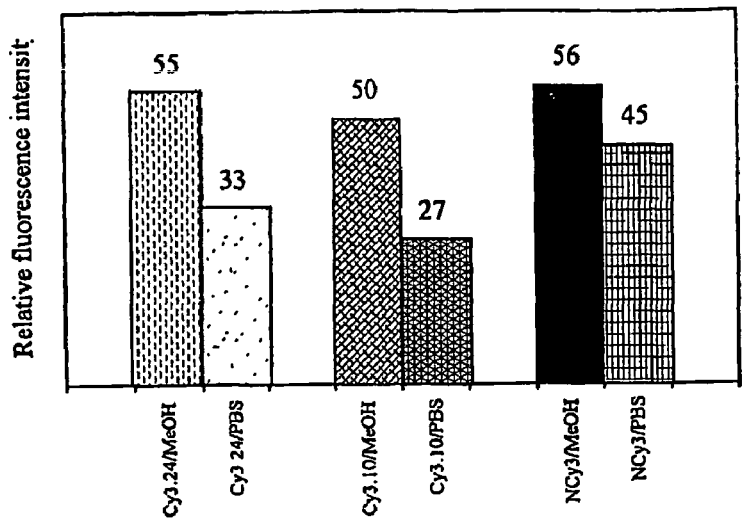
FIG. 6: Relative fluorescence intensities of non-sulfonated Cy3 isomers NCy3, Cy3.10 and Cy3.24. The absorbance for all dyes in methanol and PBS solution at 550 nm is 0.05 and the excitation wavelength is 514 nm
Figure 6:
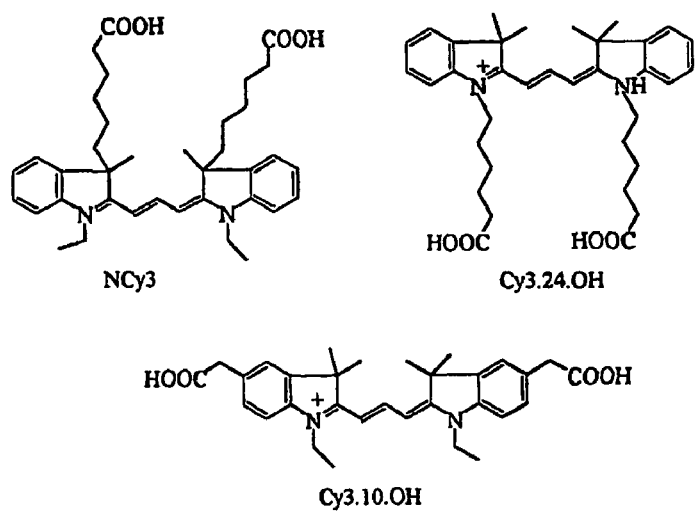
Figure 7:
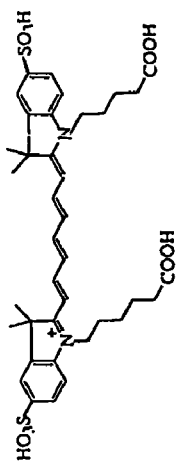
FIG. 7: Absorption spectra of Cy7.18 free acid (dotted line) and its IgG conjugate (solid line) are shown in (A). Absorption spectra of NCy7 free acid (dotted line) and its IgG conjugates (solid line) are shown in (B). NSCy7 showed less dye-dye aggregation (indicated by low vibronic shoulder).
Figure 7:
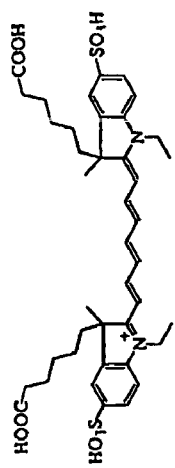
Figure 7:
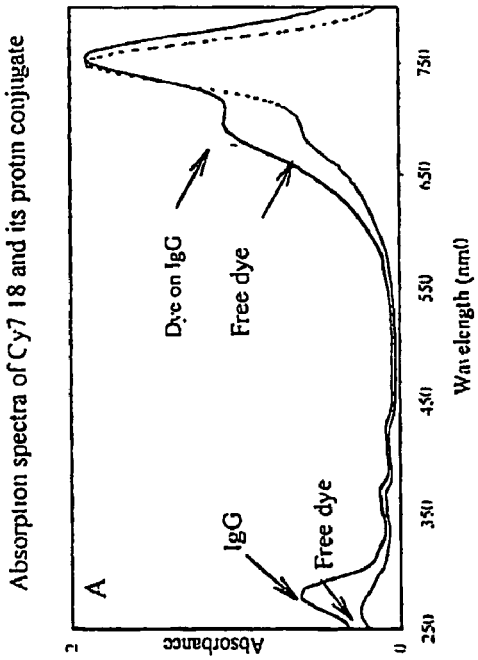
Figure 7:
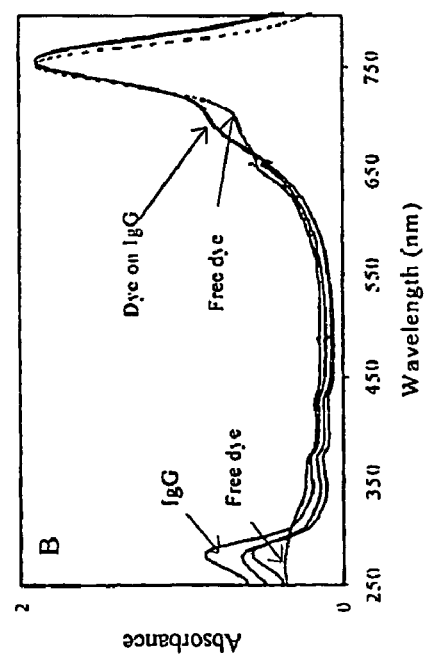
Figure 8:
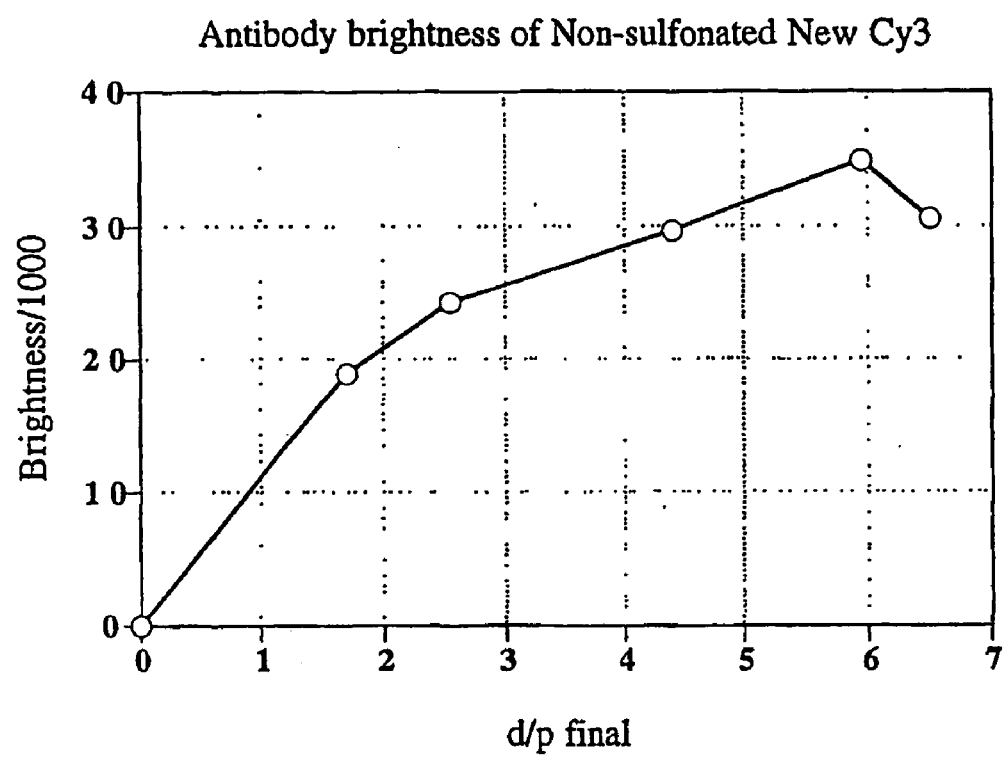
FIG. 8: Antibody brightness of NCy3. The brightness is a product of number of dyes per protein, extinction coefficient of the dye and quantum yield of the dye/antibody conjugates.
Figure 9:
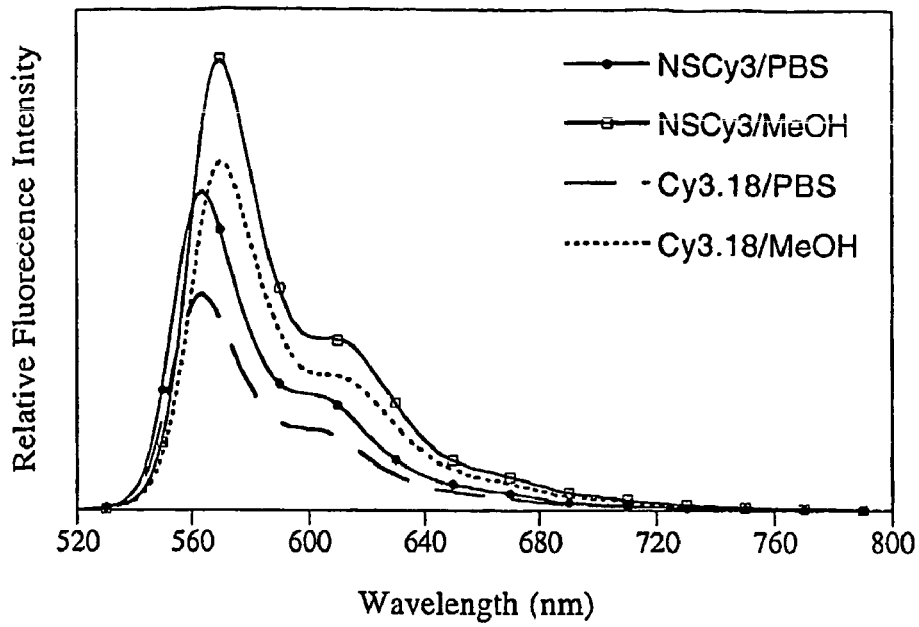
FIG. 9: is a graph showing the emission spectra of Cy3.18.OH and the disulfonated dye (NSCy3) in methanol and phosphate buffer solution when solutions of equal concentrations were excited at 514 nm. NSCy3 is 20-25% brighter than Cy3.18 in both solutions.
Figure 9:
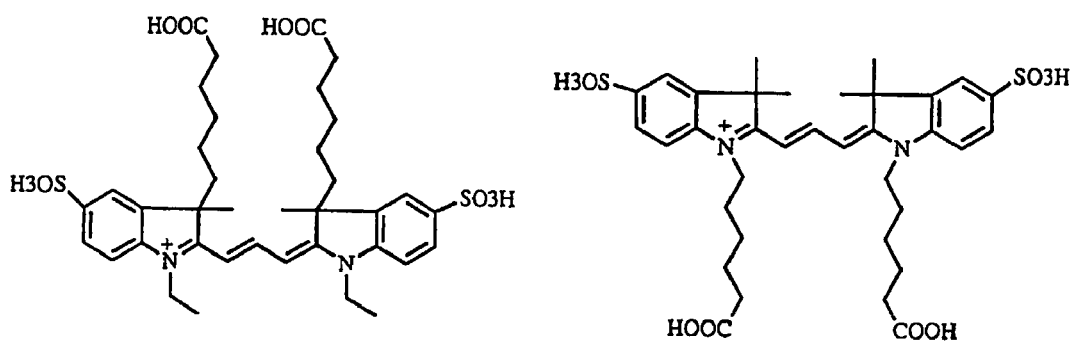

The present invention provides molecules, such as compounds of formula (I)

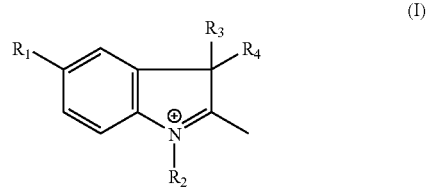

which include a reactive or water solubilizing site at R$_3$ and/or R$_4$ in structure (I)

The present invention further provides a method of synthesizing, and synthesized ketones and indolenines wherein substituent R$_3$ may be —(CH$_2$)$_{t1}$A and substituent R$_4$ may be —(CH$_2$)$_{t2}$B, wherein t$_1$ and t$_2$ are an integer, preferably from 1-22, and A and B are independently selected from —COOH, —NH$_2$, —SO$_3$, —OH, H and halogens as shown in (II).

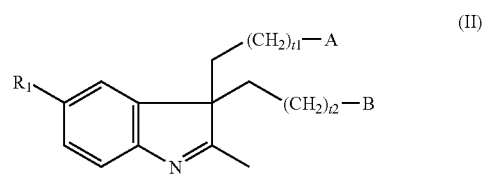

The present invention also provides a method of synthesizing ketones and indolenines wherein R$_3$ and/or R$_4$, of formula (I) for example, is —(CH$_2$)$_t$CH$_3$, wherein t is an integer in the range of 0-22, preferably 16 to 22, to produce long alkyl chain dyes as membrane potential probes.

The present invention further relates to the synthesis of cyanine, merocyanine and styryl dyes that can be modified to create covalent labeling reagents dyes, such as shown herein, wherein functional or water solubilizing groups may be included.

The present invention therefore, provides intermediates for, and methods of synthesizing cyanine, merocyanine and styryl dyes, such as those shown below.

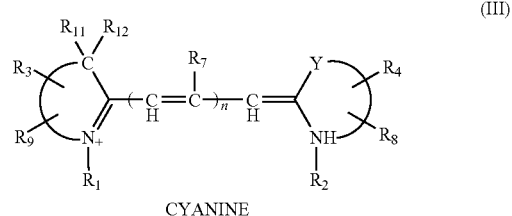

CYANINE

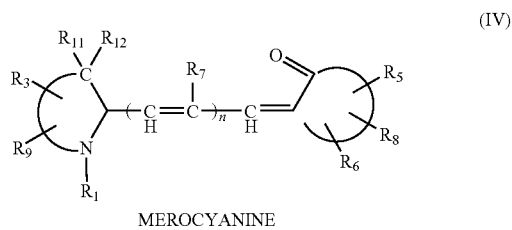

MEROCYANINE

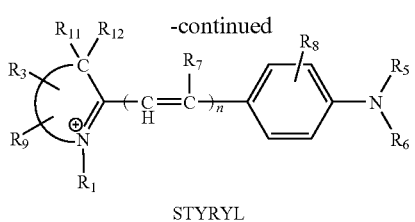

STYRYL (V)

More specifically, the intermediates of the present invention provide methods of synthesizing intermediates and synthesed compounds from the same, such as the following polymethine cyanine type dyes:

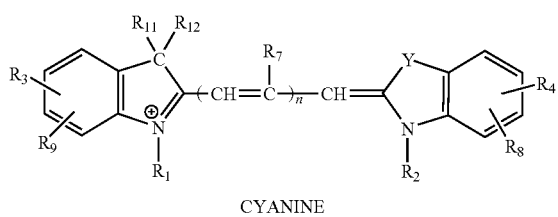

CYANINE (VI)

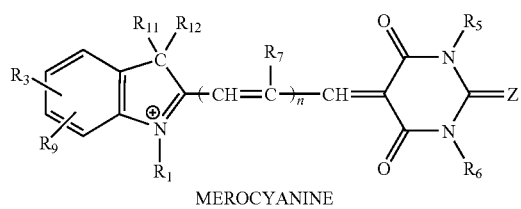

MEROCYANINE (VII)

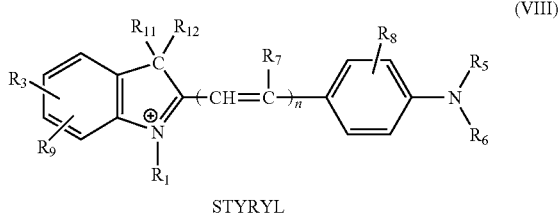

STYRYL (VIII)

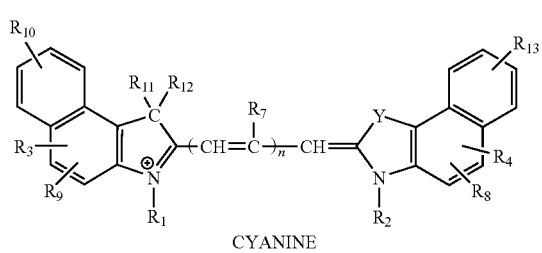

CYANINE (IX)

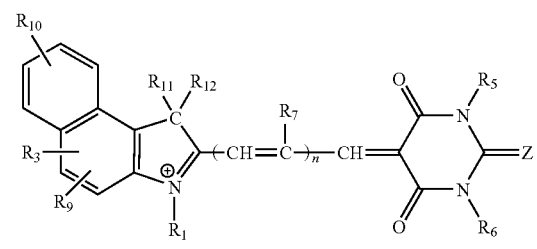

MEROCYANINE (X)

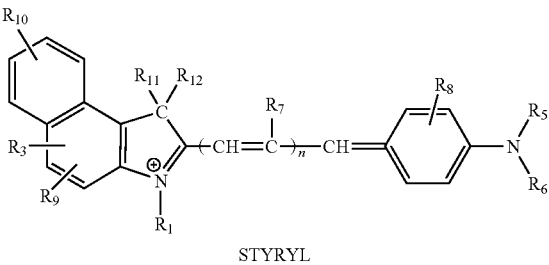

STYRYL (XI)

In these structures, Y is selected from the group consisting of O, S, —CH═CH—, >C(CH$_3$)$_2$,

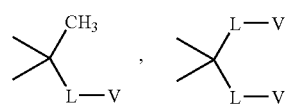

and >N—(CH$_2$)$_{1-10}$R$_{14}$, wherein R$_{14}$ is selected from —COOH, —NH$_2$, —SO$_3$$^-$, —OH and halogen;

Z is selected from the group consisting of O and S; and n is an integer selected from the group consisting of 1, 2, 3 and 4.

At least one, preferably only one, and possibly two or more of the R$_1$, R$_2$, R$_3$, R$_4$, R$_5$, R$_6$, R$_7$, R$_{11}$, and R$_{12}$ groups in each molecule is a reactive group for attaching the dye to the labeled component. A reactive group of a compound according to formula (XIII) or (XIV) can react under suitable conditions with a complementary functional group of a component, such that the component becomes covalently labelled with the compound. For certain reagents, at least one of the R$_1$, R$_2$, R$_3$, R$_4$, R$_5$, R$_6$, R$_7$, R$_{11}$, and R$_{12}$ groups on each molecule may also be a group that increases the solubility of the chromophore, or affects the selectivity of labeling of the labeled component or affects the position of labeling of the component by the dye.

In the above formulas, at least one of said R$_8$ (if any), R$_9$ (if any) and R$_{10}$ (if any) and R$_{13}$ (if any) groups comprises at least one sulfonate group. The term sulfonate is meant to include sulfonic acid because the sulfonate group is merely ionized sulfonic acid.

Reactive groups that may be attached directly or indirectly to the chromophore to form the R$_1$, R$_2$, R$_3$, R$_4$, R$_5$, R$_6$, R$_7$, R$_{11}$, and R$_{12}$ groups may include reactive moieties such as groups containing isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal and aldehyde.

Halogen and halo groups are selected from fluorine, chlorine, bromine and iodine.

Specific examples of the R$_1$, R$_2$, R$_3$, R$_4$, R$_5$, R$_6$, R$_7$, R$_{11}$, and R$_{12}$ groups that are especially useful for labeling components with available amino-, hydroxy-, and sulfhydryl groups include:

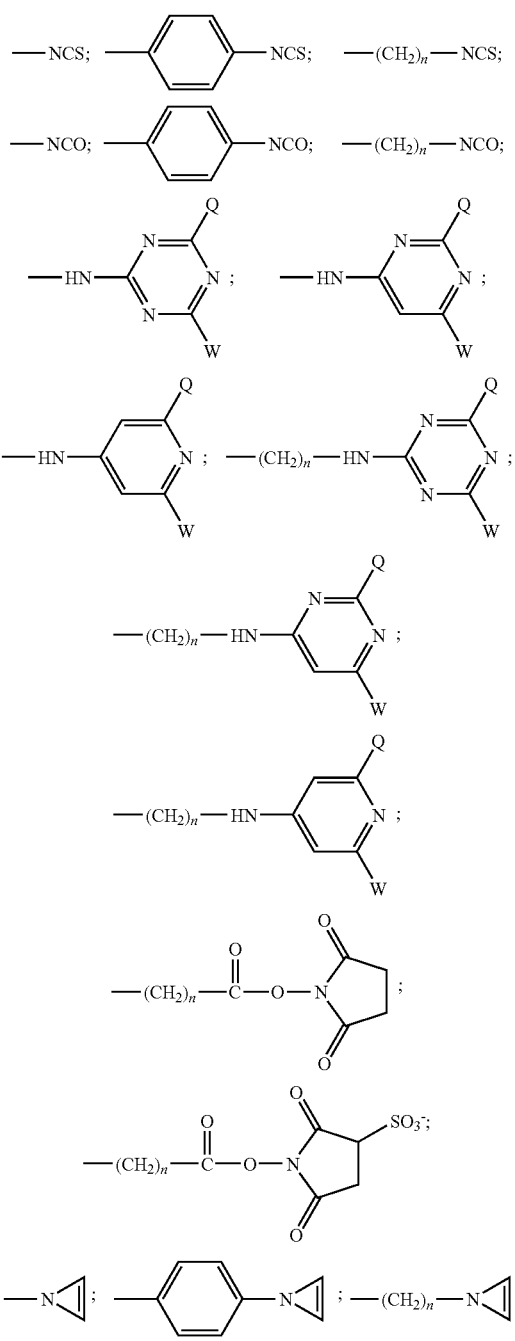

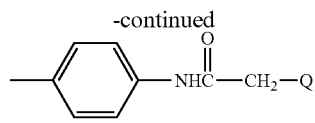

where Q is a leaving group such as I, Br, Cl.

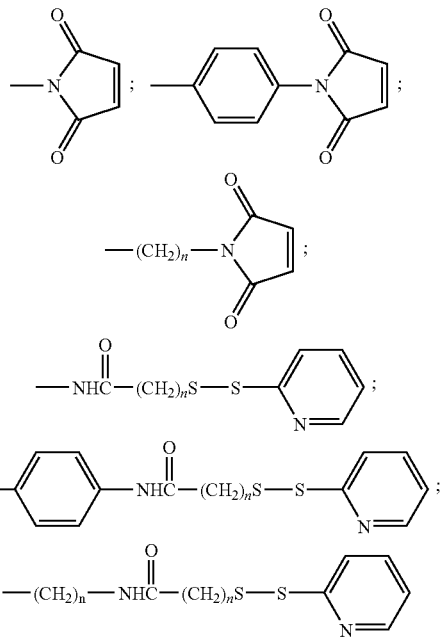

where n is an integer from 1-10.

Specific examples of $R_1$, $R_2$, $R_3$, $R_4$, $R_5$, $R_6$, $R_7$, $R_{11}$, and $R_{12}$ groups that are especially useful for labeling components by light-activated cross linking include:

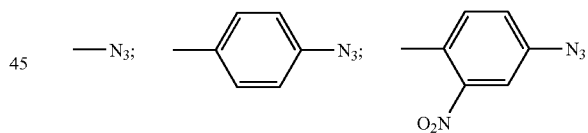

For the purpose of increasing water solubility or reducing unwanted nonspecific binding of the labeled component to inappropriate components in a sample or to reduce the interactions between two or more reactive chromophores on the labeled component which might lead to quenching of fluorescence, any of the $R_1$, $R_2$, $R_3$, $R_4$, $R_5$, $R_6$, $R_7$, $R_{11}$, and $R_{12}$ groups can be selected from the well known polar and electrically charged chemical groups. Examples are -E-F where F is hydroxy, sulfonate, sulfate, carboxylate, substituted amino or quaternary amino and where E is a spacer group such as —$(CH_2)_n$— where n is 0, 1, 2, 3 or 4. Useful examples include alkyl sulfonate; —$(CH_2)_3$—$SO_3^-$; and —$(CH_2)_4$—$SO_3^-$.

The polymethine chain of the luminescent dyes of this invention may also contain one or more cyclic chemical groups that form bridges between two or more of the carbon atoms of the polymethine chain. These bridges might serve to increase the chemical or photo-stability of the dye and might be used to alter the absorption and emission wavelength of the where n is 0 or an integer from 1-10, and at least one of Q or W is a leaving group such as I, Br, Cl.

Specific examples of $R_1$, $R_2$, $R_3$, $R_4$, $R_5$, $R_6$, $R_7$, $R_{11}$, and $R_{12}$ groups that are especially useful for labeling components with available sulfhydryls which can be used for labeling antibodies in a two-step process:

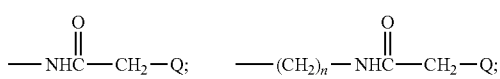

dye or change its extinction coefficient or quantum yield. Improved solubility properties may be obtained by this modification.

The present invention provides compounds of the following general formula (XII):

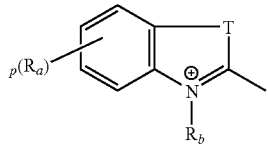
(XII)

wherein:
$R_a$ and $R_b$ are independently selected from V or L-V where
  L is a $C_{1-22}$, such as a $C_{16-21}$, straight or branched alkyl chain, optionally containing 0, 1 or 2 unsaturations or unsaturated pendent or interchain groups selected from alkenyl, alkynyl and aryl groups; and
  V is selected from hydrogen, halogen, —OH, —NH$_2$, —SH, —CN, trifluoromethyl, —SO$_3^-$ phosphate, phosphonate, quaternary ammonium, —NO$_2$, mono- or di-nitro-substituted benzyl, —COOH, and —NHCOR$_g$, where R$_g$ is C$_{1-20}$ straight or branched alkyl; a target bonding group, reactive group, reactive moiety, or NHR$_h$ where R$_h$ is H, C$_{1-20}$ straight or branched alkyl or COOH;
T is

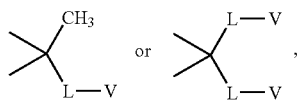

wherein each L and V are independently as defined above; and p is 0 or an integer from 1-4.

The scope of reactive groups, reactive moieties and target bonding groups described and used herein will be appreciated from the present disclosure as well as, for example, U.S. Pat. No. 6,133,445 and WO 02/26891, the entire contents of each of which is incorporated herein by reference.

The present invention provides pH sensitive cyanines of the following formula (XIII):

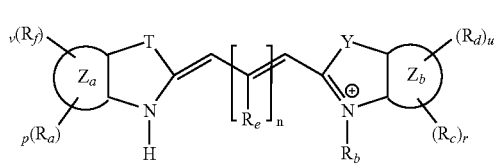
(XIII)

wherein $R_a$, $R_d$, $R_e$ and $R_f$ are any $R_a$ as defined above; Y, T and $R_b$ are as defined above;
$Z_a$ and $Z_b$ are independently, fused

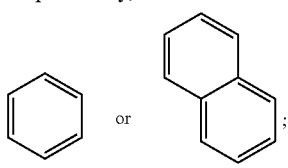

and n is an integer from 1-4. Preferably, n is an integer from 1-3.

The present invention further provides compounds of the following formula (XIV) wherein $R_a$, $R_c$, $R_d$, $R_f$, T, Y, $Z_a$ and $Z_b$ are as defined above.

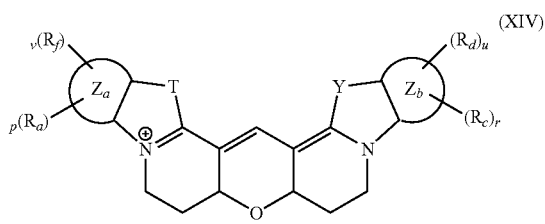
(XIV)

More than one $R_a$ may be contained on the noted ring and each such substituent may be the same or different. In one embodiment, $R_a$ is a sulfonate group and p is 1, where sulfonate includes sulfonic acid as the sulfonate group is merely an ionized sulfonic acid. Where $Z_a$ and $Z_b$ are fused rings, $R_a$, $R_c$, $R_d$ and $R_f$ may be substituted around either ring and p, u, r and v are each independently an integer from 0-4.

In the above formulas, the number of methine groups determines, in part the excitation color. The cyclic azine structures can also determine in part the excitation color. Often, higher values of n contribute to increased luminescence and absorbance. At values of n above 4, the compound becomes unstable. Thereupon, further luminescence can be imparted by modifications at the ring structures. When n=2, the excitation wavelength is about 650 nm and the compound is very fluorescent. Maximum emission wavelengths are generally 15-100 nm greater than maximum excitation wavelengths.

The present invention relates to the other substituents, such as $R_2$=H, and n is an integer from 0 to 4, in structure (I), which may be used to produce pH sensitive cyanine dyes, such as those described in copending U.S. patent application Ser. No. 09/589,502, filed Jun. 8, 2000, which is incorporated herein by reference and discloses, for example, compounds similar but distinguishable from the following formula (XV).

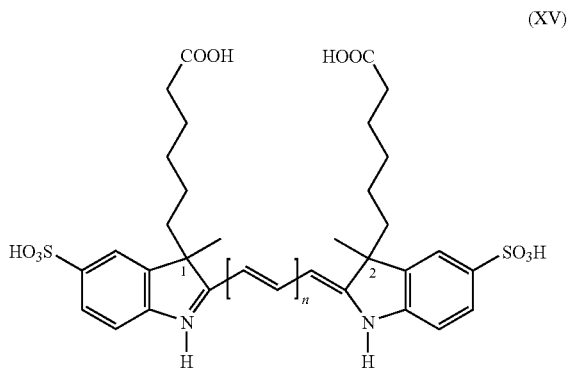
(XV)

Specifically, for example, the corresponding compounds of the related application define the substituents at positions 1 and 2 of formula (XV) as >C(C$_1$-C$_4$alkyl)$_2$, sulfur or oxygen.

The present invention further provides dyes, such as the following rigid trimethine cyanine dyes. Similar but distinct compounds are described in the U.S. Pat. No. 6,133,445. Compounds of the present invention include, for example, compounds of the following formula (XVI), intermediates and methods for synthesizing the same.

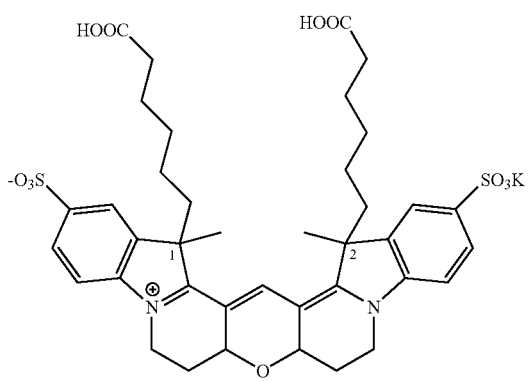

The corresponding, yet distinct, compounds of U.S. Pat. No. 6,133,445 define the substituents at positions 1 and 2 of formula (XVI) as the same or different and selected from iii) 2-{(1E,3E,5E)-5-[3-(5-carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium (Example 15);

iv) 3-(5-carboxypentyl)-2-[(1E,3E,5E)-5-(7-chloro-3,3-dimethyl-5-sulfo-1,3-dihydro-2H-indol-2-ylidene)penta-1,3-dienyl]-3-methyl-5-sulfo-1-(4-sulfobutyl)-3H-indolium (Example 16);

v) 3-(5-carboxypentyl)-3-methyl-2-{(1E,3E,5E)-5-[3-methyl-5-sulfo-3-(4-sulfobutyl)-1,3-dihydro-2H-indol-2-ylidene]penta-1,3-dienyl}-5-sulfo-1-(4-sulfobutyl)-3H-indolium (Example 17); and vi) 6,7,9,10-tetrahydro-2,14-disulphonato-16,16,18-trimethyl-7aH,8aH-bisindolinium[3,2-a,3'2'-a]pyrano[3,2-c;5,6-c']dipyridin-5-ium-18-hexanoic acid (Example 19).

The present invention relates to the energy transfer dyes wherein cyanine-cyanine dye conjugates are synthesized such as (XVII). Such cyanine-cyanine dye complexes have been described in the U.S. Pat. Nos. 6,008,373 and 6,130,094.

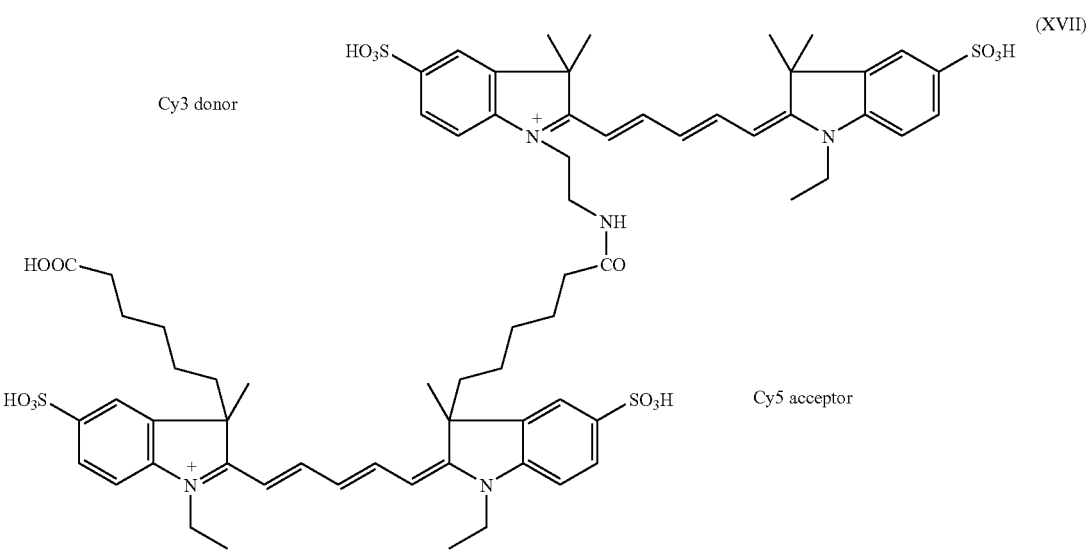

bis-$C_1$-$C_4$ alkyl and $C_4$-$C_5$ Spiro alkyl substituted carbon, oxygen, sulphur, selenium, CH=CH, and N—W wherein N is nitrogen and W is selected from hydrogen, a group —$(CH_2)_n R^{12}$ where n is an integer from 1 to 26 and $R^{12}$ is selected from hydrogen, amino, aldehyde, acetal, ketal, halo, cyano, aryl, heteroaryl, hydroxyl, sulphonate, sulphate, carboxylate, substituted amino, quaternary amino, nitro, primary amide, substituted amide, and groups reactive with amino, hydroxyl, carbonyl, phosphoryl, and sulphydryl groups. Compounds of the present invention are other than those disclosed in U.S. Pat. No. 6,133,445.

Exemplary dyes according to the invention are as follows:

i) 2-{(1E,3E,5E)-5-[3-(5-carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium (Example 13);

ii) 3-(5-carboxypentyl)-2-[(1E,3E,5E)-5-(5,7-dichloro-3,3-dimethyl-1,3-dihydro-2H-indol-2-ylidene)penta-1,3-dienyl]-3-methyl-5-sulfo-1-(4-sulfobutyl)-3H-indolium (Example 14);

Target bonding groups, reactive groups and reactive moieties include, amine, hydroxy, thiol, N-hydroxy-succinimidyl ester, N-hydroxy-sulfosuccinimidyl ester, isothiocyanate, anhydride, haloacetamide, isocyanate, monochlorotriazine, dichlorotriazine, optionally substituted pyridine, mono- or di-halogen substituted diazine, maleimide, aziridine, imidoester, alkylimidate, hydrazide carbodiimide, azidonitrophenyl, azide, 3-(2-pyridyl dithioyproprionamide, glyoxal, aldehyde, maleimide, sulphonyl halide, phosphoramidite, acid halide, hydrazine and carbodimide groups, and groups reactive with amino, hydroxyl, aldehyde, phosphoryl, or sulphydryl groups which are, for example, covalently attached to proteins, nucleic acids, nucleosides, nucleotides, carbohydrates, sugars, cells, and combinations thereof, and other biological and non-biological materials, to make the same fluorescent and detectable, as described, for example in U.S. Pat. No. 6,048,982.

V may also be a group which increases the solubility of the chromophone or affects the selectivity of labeling of the ultimately labeled component or affects the position of labeling of the labeled component by the dye.

The compounds or dyes of the present invention may be used to label, for example avidin, streptavidin, antibodies, DNA, RNA, nucleosides, nucleotides or lectins to detect, measure and/or quantify, for example, biotinylated materials, antigens, haptens, carbohydrate groups, DNA, RNA and complementary DNA or RNA, such as described therein.

In another embodiment, the present invention provides a component-labeled complex wherein the label is a compound of any one of formulas (III)-(XVII) and the component is an antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, non-cellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor.

A cyanine dye or its derivative of the present invention preferably absorbs v maximally in the range of 400-950 nm, preferably in the range of 420-470 nm, 520-580 nm, 640-680 nm, 740-790 nm or 820-850 nm. In yet another embodiment, the present invention provides a method of fluorescent detection wherein the dye or derivative of the present invention is detected or when multiple fluorescent dyes are used, a dye or derivative of the present invention may be used in conjunction with dyes which do not either fluoresce at the same or similar pH conditions and/or at the wavelengths of the presently provided dyes or derivatives.

In a further embodiment, the compound of formula (XIII) may be used in a fluorescence method for the qualitative and/or quantitative detection of pH. The method comprises contacting or mixing a dye of formula (XIII) with a composition containing cells, tissues or biological fluid, and detecting the emitted fluorescence. The presence of a fluorescent signal is indicative of an acidic environment. In one embodiment, the method may be used for detecting intracellular environments, such as may be contained in subcellular compartments or structures. Compounds of formula (XIII) or their membrane permeant derivatives may be actively or passively absorbed by cells where they may be detected by fluorescence detection. One of ordinary skill will appreciate the variability of cell permeability properties of compounds according to formula (XIII) and will be able to routinely test for the same.

The methods according to the present invention may employ known devices for illumination and detection at separate defined wavelengths. Such devices include fluorescence spectrophotometers, fluorescence microscopes. Alternatively, changes in fluorescence intensity may be measured by means of a charge coupled device (CCD) imager (such as a scanning imager or an area imager) to image all of the wells of a microtitre plate.

The present invention is further described by the following examples.

EXAMPLES

1. Synthesis of diethyl 2-acetyl-2-methyloctane-1,8-dioate

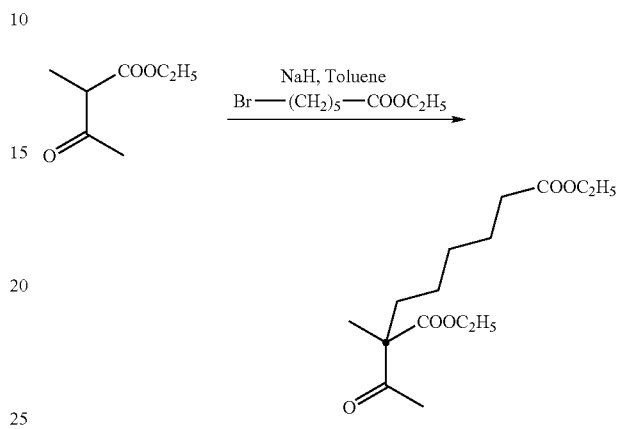

In a 1 L three necked flask equipped with a mechanical stirrer and reflux condenser was placed dry toluene (300 ml). The system was flushed with argon and sodium hydride (Aldrich, 60% dispersion in mineral oil) (7.2 g, 0.18 mmol) was added. Ethyl-γ-methylacetoacetate (Aldrich, 21 g, 0.15 mole) was added with stirring over a 30 minutes. The resulting solution was heated under reflux for 2 hrs and cooled slightly. (Note: Reaction mixture becomes a thick paste and mechanical stirrer is essential). Ethyl 6-bromohexanoate (Aldrich, 33.5 g, 0.15 mol) was added (all at once) and the suspension was heated under reflux for 12 hrs, cooled, filtered and the solvent evaporated under pressure. The residue was distilled under vacuum to yield 20 g (46%) of colorless liquid, b.p. 110-115° C. (0.1 mm). IR (neat): vcm$^{-1}$=1735 (s) and 1713 (s). $^1$H NMR in CDCl$_3$ δ, 4.1-4.2 (m, 4H, (O—CH$_2$)$_2$); 2.1 (t, J=8.4 Hz, 2H, CH$_2$COO—); 2.15(s, 3H, CH$_3$CO); 1.5-2.0 (m, 4H, (CH$_2$)$_2$); 1.2-1.4 (m, 13H, 2 CH$_2$ and three —CH$_3$).

2. Synthesis of 7-acetyloctanoic acid (or 7-methyl-8-oxononanoic acid)

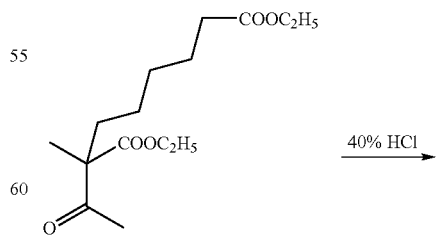

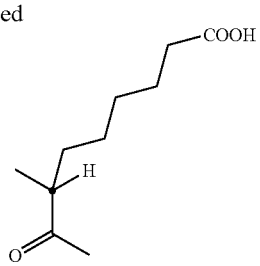

A mixture of diester from Example 1 (15 g, 0.052 mol) in dilute hydrochloric acid (40-50%) (100 ml) was heated to reflux for 12 hrs. The reaction mixture was cooled and extracted with ethyl acetate (3×100 ml). The organic phase was dried over sodium sulfate, filtered, and ethyl acetate was removed. The residue was distilled under reduced pressure, to yield 7.7 g (80%), colorless liquid, b.p. 120-125° C., IR (neat): $vcm^-$=1736 (s) and 1710 (s). $^1$H NMR, CDCl$_3$, δ, 2.45-2.55 (q, 1H, J=6.6 Hz, 7-H); 2.35 (t, J=7.3 Hz, 2H, —CH$_2$—COOH); 2.125 (s, 3H, COCH$_3$); 1.65-1.1.75 (m, 2H, —CH$_2$); 1.23-1.4 (m, 6H, (—CH$_2$)$_3$); 1.1 (d, J=5.9 Hz, 7-CH$_3$).

3. Synthesis of 6-(2,3-dimethyl-3H-indol-3-yl)hexanoic acid

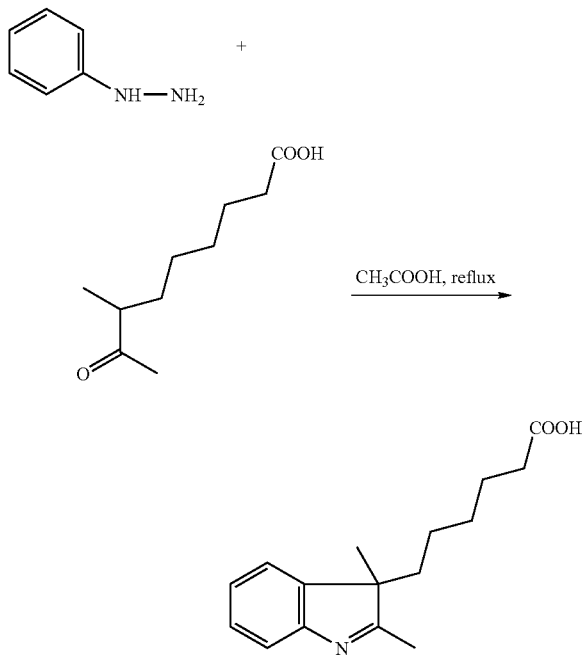

To a stirred solution of phenylhydrazine hydrochloride (Aldrich, 7.2 g, 0.05 mol) in acetic acid (50 ml) was added 7-acetyloctanoic acid (11 g, 0.06 mol). The reaction mixture was heated under reflux for 4 hrs. The solution was cooled. (No clear precipitate was observed). Acetic acid was removed under reduced pressure. The resulting yellow liquid was chromatographed on a silica gel column using chloroform/methanol mixture as solvent. Pure 6-(2,3-dimethyl-3H-indol-3-yl) hexanoic acid (8.0 g, 61%) was obtained as pale yellow oil which crystallized on standing, m.p. 115-118° C.; IR $vcm^{-1}$=2927, 2860, 2526, and 1709. $^1$H NMR, CDCl$_3$, δ, 7.6 (d, 1H, J=7 Hz, 4-H); 7.2-7.4 (m, 3H, aromatic protons); 2.25 (s, 3H, —CH$_3$); 2.1-2.2(t, —CH$_2$COOH); 1.72-1.94 (m 2H, —CH$_2$); 1.4-1.45 (m, 2H, —CH$_2$); 1.23-1.05 (m, singlet merged in m, 5H, —CH$_2$, —CH$_3$); 0.55-0.85 (m, 2H, —CH$_2$). TLC, Rf=0.22 (silica gel, methanol-chloroform, 5:95).

4. Synthesis of 3-(5-carboxypentyl)-2-{(1E,3E)-3-[3-(5-carboxypentyl)-1-ethyl-3-methyl-1,3-dihydro-2H-indol-2-ylidene]prop-1-enyl}-1-ethyl-3-methyl-3H-indolium iodide (NCy3)

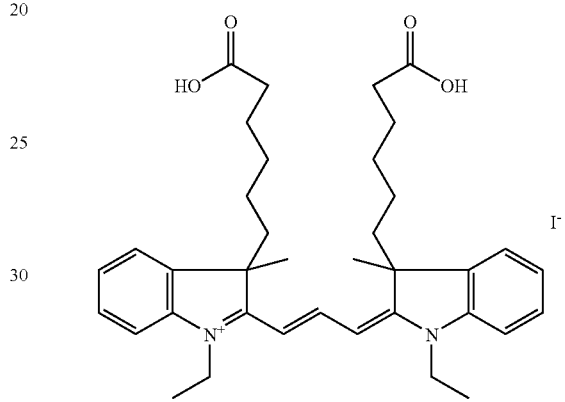

4.1 3-(5-Carboxypentyl)-1-ethyl-2,3-dimethyl-3H-indolium iodide 6-(2,3-Dimethyl-3-hydroindole-3-yl)hexanoic acid (518 mg, 2 mmol) was suspended in acetonitrile (5 ml) and ethyl iodide (1.2 g, 10 mmol) and the mixture was heated to reflux with stirring for 1 hr. More ethyl iodide (2 g) was added and heating continued for an additional 12 hrs. The mixture was then cooled, and acetonitrile and excess ethyl iodide were removed on a rotary evaporator. The sticky mass was washed several times with ice-cooled diethyl ether and dried to yield pink amorphous powder (0.45 g, 78%). The product was used for the next reaction without further purification.

4.2 To a stirred solution of 6-(1 ethyl-2,3-dimethyl-3-hydroindol-3-yl)hexanoic acid (288 mg, 0.95 mmol) in pyridine (10 ml) at 120° C. was added dropwise, triethyl orthoformate (100 mg, 67 mmol) over 30 minutes. After 2 hrs the reaction mixture was cooled and triturated with diethyl ether. The product was purified on a silica gel column using chloroform/methanol mixture as solvent. The major compound (Rf=0.45, tlc, silica gel, methanol in chloroform 5%) was obtained as a pink solid (251 mg, 35%); $^1$H NMR, CDCl$_3$, d, 8.2 (t, H, J=7Hz, (β-H); 7.1-7.6 (m, 8H, aromatic; 6.4 (d, 2H, J=7 Hz, α-H, α'-H); 4.2 (m, 4H, 2-NCH$_2$); 2.2-2.3 (m, 4H, 2-CH$_2$COOH, 2-CH$_2$); 1.8 (s, 6H, (—CH$_3$)$_2$); 1.43 (t, 6H, J=6.5 Hz, 2-CH$_3$); 1.1-1.2 (m, 4H, 2-CH$_2$); 0.5-0.7 (m, 4H, 2-CH$_2$); λmax: 550 nm, methanol.

5. Preparation of 6-(2,3-dimethyl-5-sulfo-3H-indol-3-yl)hexanoic acid

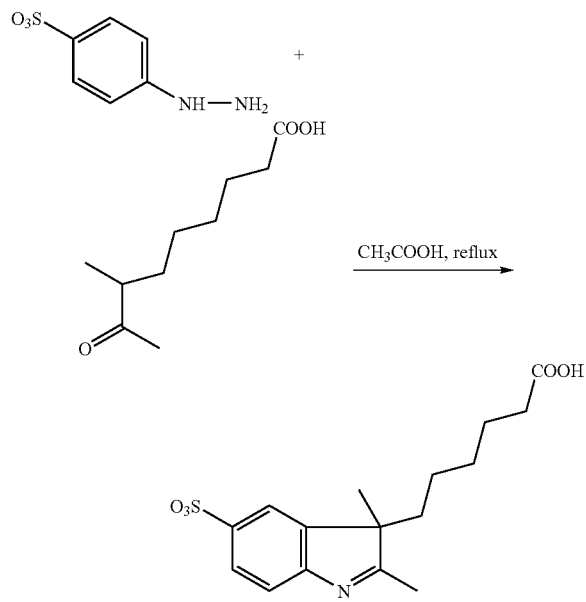

To a stirred solution of 4-hydrazinobenzenesulfonic acid (Aldrich, 11.25 g, 0.06 mol) in acetic acid (50 ml) was added 7-acetyloctanoic acid (16.7 g, 0.09 mol). The reaction mixture was heated under reflux for 12 hrs. Acetic acid was removed under reduced pressure. The resulting solid was dissolved in methanol and reprecipitated with a saturated solution of potassium hydroxide in isopropanol. The solid was filtered, washed with isopropanol and dried, (8 g, 40%). The analytical sample was obtained by C18 reversed phase column chromatography using water/methanol mixture as solvent., m.p. 250° C. dec; IR vcm$^{-1}$=2930, 2597, and 1719. $^1$H NMR, D$_2$O, δ, 7.8-7.9 (m, 2H, 4-H and 6-H of aromatic protons); 7.6 (d, J=7 Hz, 1H, 7-H of aromatic); 2.2 (t, J=7 Hz, 2H, —CH$_2$—COOH); 1.9-2.1 (m, 2H, alkyl); 1.2-1.6 (a singlet merged in a multiplet, 7H, —CH$_3$ & (—CH$_2$)$_2$); 0.6-0.9 (m, 2H, alkyl).

6. Synthesis of 3-(5-carboxypentyl)-2-{(1E,3E)-3-[3-(5-carboxypentyl)-1-ethyl-3-methyl-5-sulfo-1,3-dihydro-2H-indol-2-ylidene]prop-1-enyl}-1-ethyl-3-methyl-3H-indolium-5-sulfonate (NSCy3)

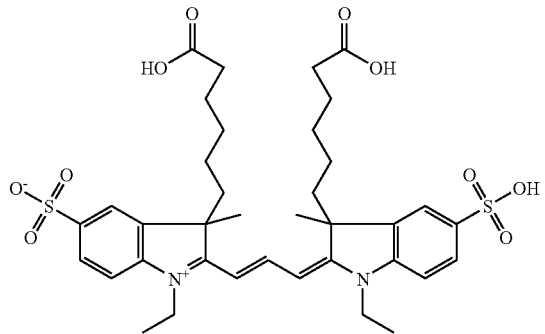

3-(5-Carboxypentyl)1-ethyl-2,3-dimethyl-3H-indolium-5-sulfonate was synthesized following the procedure described in Example 4.1. 6-(2,3-Dimethyl-5-sulfo-3-hydroindole-3-yl)hexanoic acid (680 mg, 2 mmol) was suspended in acetonitrile (10 ml) and ethyl iodide (1.2 g, 10 mmol) and the mixture was heated to reflux with stirring for 1 hr. More ethyl iodide (2 g) was added and heating continued for additional 12 hrs. The mixture was then cooled and solvent removed on a rotary evaporator. The sticky mass was dissolved in methanol (5 ml). A solution of potassium acetate in isopropanol was added until the reaction product was alkaline to pH. The solid obtained was filtered and washed several times with isopropanol to yield a gray amorphous powder (500 mg, 61%). The product was used for the next reaction without further purification.

To a stirred solution of 3-(5-carboxypentyl)1-ethyl-2,3-dimethyl-3H-indolium-5-sulfonate (potassium salt) (400 mg, 0.98 mmol) in pyridine (10 ml) at 100° C. was added triethyl orthoformate (100 mg, 66 mmol) over 30 minutes. After 2 hours the reaction mixture was cooled and diluted with several volumes diethyl ether. A product separated as red powder from which supernatant fluid was removed by decantation. It was dissolved in methanol and reprecipitated with isopropanol containing potassium acetate. The crude dye was collected on a filter paper and dried (380 mg, 90%). It was purified by C18, column chromatography using water-methanol mixture for elution. A pure dye was obtained as pink solid (251 mg), λmax 555 nm; $^1$H NMR (D$_2$O) δ, 8.42 (t, 1H, J=13 Hz, β-H of the bridge); 7.6-7.8 (m, 4H, 4-H, 4'-H, 6-H, 6'-4); 7.2 (d, 2H, J=7.7 Hz, 7-H, 7'-H); 6.5 (d, 2H, J=13 Hz, α, α'-H); 4.1 (broad signal, 4H, (N—CH$_2$)$_2$); 1.8-2.2 (m, 8H, alkyl and CH$_2$COOH); 1.2-1.7 (m, 24H, 6-CH$_2$, 4-CH$_3$); 0.45-0.8 (m, 4H, alkyl).

7. Synthesis of ethyl 2-acetyl-7-acetyloxy-2-methylheptanoate

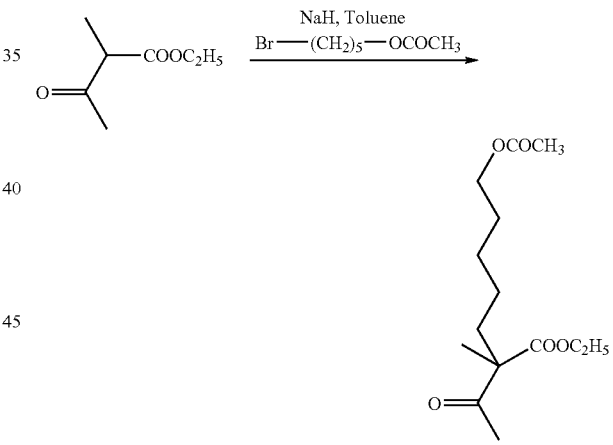

In a 1 L three necked flask equipped with a mechanical stirrer and reflux condenser was placed dry toluene (300 ml). The system was flushed with argon and sodium hydride (Aldrich, 60% dispersion in mineral oil) (7.2 g, 1.2 eq.) was added. Ethyl-α-methylacetoacetate (Aldrich, 21 g, 0.15 mole) was added with stirring over a 30 minutes. The resulting solution was heated under reflux for 2 hours and cooled slightly. (Note: Reaction mixture becomes a thick paste and a mechanical stirrer is essential). 5-Bromopentylacetate (Aldrich, 31.5 g, 15 mol) was added (all at once) and the suspension was heated under reflux for 12 hr, cooled, filtered and the solvent evaporated under reduced pressure. The residue was distilled under vacuum to yield 20 g (45%) of colorless liquid, b.p 90-92 (0.5 mm). $^1$H NMR in CDCl3 δ, 4.1-4.2 (m, 2H, O—CH$_2$CH$_3$); 3.5 (t, J=7 Hz, 2H, CH$_2$OCO—); 2.2 (s, 3H, CH$_3$CO); 2.1 (s, 3H, —COCH$_3$); 1.5-2.0 (m, 10H, 4-(CH$_2$)$_2$, C—CH$_3$, OCH$_2$CH$_3$).

8. Synthesis of 8-hydroxy-3-methyloctan-2-one or 6-acetyl-octanol

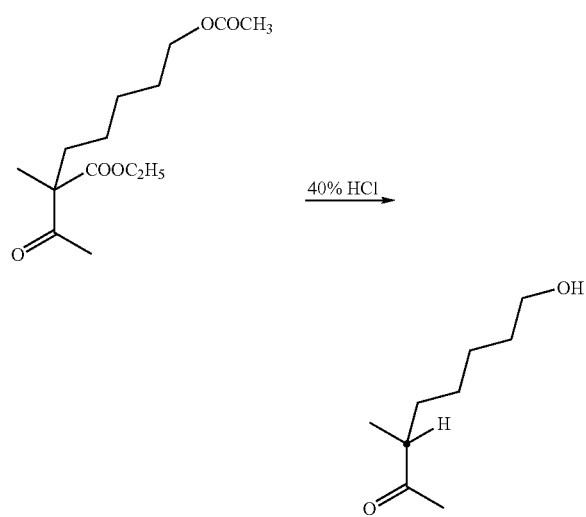

A mixture of diester (15 g, 0.06 mol) in a dilute hydrochloric acid (40-50%) (2100 ml) was heated to reflux for 12 hrs. The reaction mixture was cooled and extracted with ethyl acetate (3×100 ml). The organic phase was dried over sodium sulfate, filtered, and ethylacetate was removed. The residue was distilled in vacuum, to yield 7.19 g (80%) colorless liquid, b.p. 90-97° C. at 0.7 mm, IR (neat): $vcm^{-1}$=1736; $^1$H NMR, $CDCl_3$, δ, 3.55 (t, 2H, J=6.6 Hz, —$CH_2OH$); 2.45 (m, 1H, 7-H); 2.15 (s, 3H, $COCH_3$); 1.65-1.82 (m, 4H, (—$CH_2$)$_2$); 1.2-1.55 (m, 4H, (—$CH_2$)$_2$); 1.1 (d, J=7.3 Hz, —CH—$\underline{CH_3}$).

9. Synthesis of 5-(2,3-dimethyl-3H-indol-3-yl)pentan-1-ol

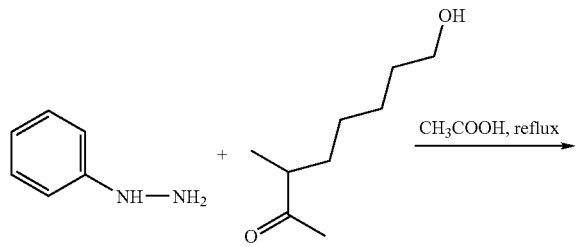

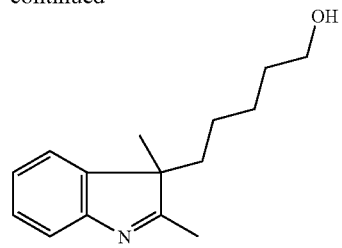

To a stirred solution of phenylhydrazine hydrochloride (Aldrich, 7.2 g, 0.05 mol) in acetic acid (50 ml) was added 8-hydroxy-3-methyloctan-2-one (12 g, 0.07 mol). The reaction mixture was heated under reflux for 4 hrs. The solution was cooled. (No clear precipitate was observed). Acetic acid was removed under reduced pressure. The resulting yellow liquid was chromatographed on a silica gel column using chloroform:methanol mixture as solvent. Pure 6-(2,3-dimethyl-3-hydroindol-3-yl)pentanol (8.0 g, 60%) was obtained as pale yellow oil; $^1$H NMR, $CDCl_3$, δ, 7.8 (d, J =7 Hz, 4-H aromatic); 7.2-7.6 (m, 3H, aromatic protons); 3.5 (t, J=6.5 Hz, —$CH_2OH$; 2.6 (s, 3H, 2-$CH_3$ of indole); 1.8-2.12 (m, 2 h, alkyl), 1.3-1.7 (singlet merged in multiplets, 7H, 2 alkyl and —$CH_3$ of indole); 0.6-0.9 (m, 2H, alkyl).

10. Synthesis of 6-(1,2-dimethyl-6,8-disulfo-1H-benzo[e]indol-1-yl)hexanoic acid

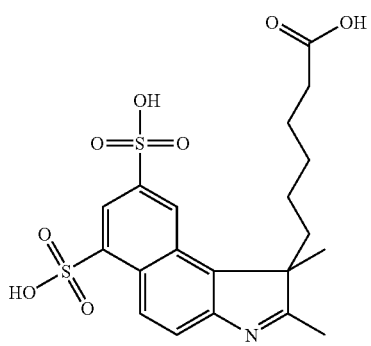

(5,7-Disulfo-2-naphthyl)hydrazinium chloride (2.0 g), 7-methyl-8-oxononanoic acid (1.5 g) and acetic acid (15 ml) were heated from 80-140° C. for a total of 24 hrs. After evaporation of the solvent under vacuum, the residue was triturated with 2-propanol to give a pink solid. This solid was collected by filtration, washed with 2-propanol, then excess diethyl ether and dried under vacuum over phosphorus pentoxide. Yield of crude product=1.96 g. This was purified as required by preparative HPLC (RPC18. Water/MeCN/TFA) to give pure product. $^1$H-nmr ($D_2O$) δ 0.25-0.4 (1H, broad m), 0.5-0.65 (1H, broad m), 1.00 (2H, m), 1.25 (2H, m), 1.78 (3H, s), 2.06 (2H, t), 2.35-2.5 (1H, broad m), 2.65-2.8 (1H, broad m), 2.90 (3H, s), 8.05 (1H, d), 8.58 (1H, d), 8.70 (1H, d) and (8.97 (1H, d). MS (LCMS) MH+470. Acc. Mass: MH+470.0931 (−2.6 ppm for $C_{20}H_{24}NO_8S_2$).

11. Synthesis of 3-(5-carboxypentyl)-2-{(1 E,3E,5E,7E)-7-[3-(5-carboxypentyl)-1-ethyl-3-methyl-5-sulfo-1,3-dihydro-2H-indol-2-ylidene]hepta-1,3,5-trienyl}-1-ethyl-3-methyl-3H-indolium-5-sulfonate (NSCy7)

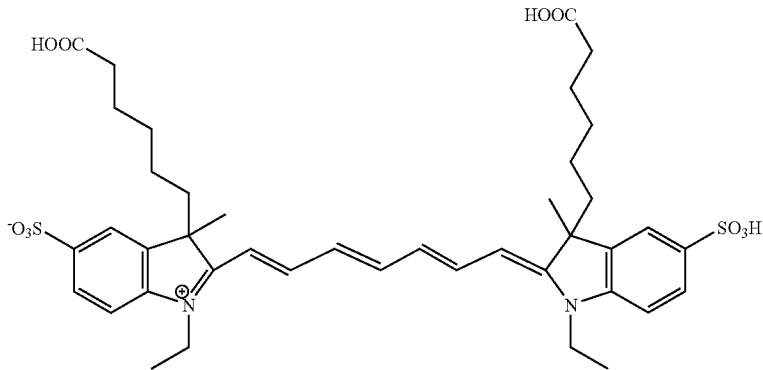

Glutaconaldehyde dianil hydrochloride (143 mg, 0.5 mmol) was dissolved in a heated mixture of acetic anhydride (4 ml) and pyridine (1 ml). The intermediate 6-(1-ethyl-2,3-dimethyl-5-sulfo-3-hydroindol-3-yl)hexanoic acid (368 mg, 1 mmol) was added and mixture was heated to reflux for an additional 10 min. and then cooled. The dye was precipitated with diethyl ether. The supernatant liquid was separated. Solid was redissolved in a minimum volume of methanol and reprecipitated with isopropanol. The purple solid was collected on a filter paper and dried (160 mg, yield 18%). The pyridinium salt was converted into its potassium salt and purified by C18 column chromatography using water-methanol mixture as eluent. λmax=750 nm.

$^1$H NMR (D$_2$O) δ, 7.7 (m, 6H, 4-H, 4'-H, 6-H, 6'-H and γγ' protons of the bridge); 7.4 (t, 1H, J=13 Hz, β-proton of the bridge): 7.2 (d, 2H, J=7.7 Hz, 7-H, 7'-H); 6.35 (t. 2H, J=13 Hz, β, and β' protons of the bridge, 6.15 (d, 2H, J=7 Hz, αα'-H); 4.1 (broad signal, 4H, (N—CH$_2$)$_2$); 1.8-2.2 (m, 8H, alkyl and CH$_2$COOH); 1.2-1.7 (m, 24H, 6-CH$_2$, 4 CH$_3$); 0.45-0.8 (m, 4H, alkyl). Rf=0.26 (RP-C18, water/methanol-7.5:2.5).

12. Succinimidyl Esters of Carboxyalkyl Cyanine Dyes

The following general procedure was used to prepare succinimidyl esters of Cy3.24.OH, Cy3.10.OH, NCy3, NSCy3, Cy7.18.OH, and NSCy7. A procedure for making succinimidyl active ester using disuccinimidyl carbonate (DSC) has been described by Ogura, H., Kobayashi, T., Keiko, S., Kawabe. K. and Takeda R. (1979) A novel active ester synthesis reagent (N,N'-Disuccinimidyl carbonate). Tetrahedron Lett. 4745-4746.

In a typical experiment carboxyalkyl indocyanine was dissolved in mixture of dry DMF (2 mL/100 mg dye) and dry pyridine (0.1 mL/100 mg dye). Disuccinimidyl carbonate (DSC) (1.5 eq/carboxyl group) was added and the mixture was stirred at 55-60° C. for 90 min. under nitrogen. After diluting the mixture with dry ethyl ether, the supernatant was decanted. The product was either washed repeatedly with solvent or dissolved in DMF and reprecipitated. Nearly quantitative yields of cyanine active esters were obtained. The formation of the active succinimidyl ester was confirmed by its reaction with benzylamine in DMF or its reaction with taurine in a pH 9.4 bicarbonate buffer. Reversed phase C18 TLC spotted with the conjugate, the succinimidyl ester and hydrolyzed carboxylate product for comparison and developed with water-methanol mixture. Since activation was sometimes incomplete, reverse-phase HPLC was also used to determine the percentage of fluorochrome in the active ester form. The sample was eluted through an Alltech Econosphere 250 mm×4.6 mm C18 RP column using a mixture of 25% acetonitrile and 75% water containing 0.1% trifluoroacetic acid. The percentages of activated and unactivated cyanine fluorohore were determined by integration of the absorbance signals from a Varian UV/VIS detector.

Alternative procedures for preparing N-hydroxysuccinimidyl esters of carboxyalkyl cyanine dyes are described hereinafter, for example, see Examples 13-16.

13. Synthesis and activation of 2-{(1E,3E,5E)-5-[3-(5-carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium

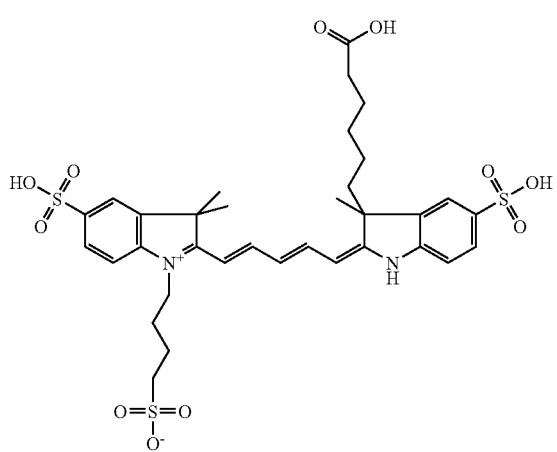

13.1
6-(2,3-Dimethyl-5-sulfo-3H-indol-3-yl)hexanoic acid

4-Hydrazinobenzenesulfonic acid (1.88 g, 10 mmol), 7-methyl-8-oxononanoic acid (2.8 g, 15 mmol) and glacial acetic acid (10 ml) were mixed and heated under reflux for 6 hrs. The solvent was then evaporated under vacuum and the residue triturated with diethyl ether until a solid was obtained.

This was dried under vacuum to give crude product, 3.4 g (100%). This was purified by preparative HPLC as required (RPC18. Water+0.1% TFA→MeCN+0.1% TFA gradient). UV/Vis (Water+0.1% TFA): 274, 229, 204 nm. $^1$H-nmr (D$_2$O) δ 0.6-0.9 (2H, broad m), 1.10-1.25 (2H, broad m), 1.35-1.50 (2H, m), 1.60 (3H, s), 2.10-2.40 (2H, broad m+2H, t), 7.77 (1H, d), 7.97 (1H, dd) and 8.06 (1H, d) MS (MALDI-TOF) MH+340.

13.2 4-(2,3,3-Trimethyl-5-sulfo-3H-indolium-1-yl) butane-1-sulfonate

A mixture of potassium 2,3,3-trimethyl-3H-indole-5-sulfonate (5.50 g, 20 mmol), 1,4-butanesultone (4.0 ml, 40 mmol) and 1,2-dichlorobenzene (100 ml) was mixed and heated at 140° C. for 24 hrs and then 175° C. for 6 hrs. After cooling, the magenta solid was collected by filtration, washed with ethyl acetate and dried under vacuum to give 7.97 g (97%) of product. Used without further purification. $^1$H-nmr (D$_2$O) δ 1.62 (6H, s), 1.9-2.0 (2H, m), 2.1-2.2 (2H, m), 2.89 (2H, t), 4.55 (2H, t), 7.98 (1H, d), 8.08 (1H, d) and 8.12 (1H, d).

13.3 4-{2-[(1E,3E)-4-Anilinobuta-1,3-dienyl]-3,3-dimethyl-5-sulfo-3H-indolium-1-yl}butane-1-sulfonate A mixture of 4-(2,3,3-trimethyl-5-sulfo-3H-indolium-1-yl)butane-1-sulfonate (6.20 g), malonaldehyde bis(phenylimine) monohydrochloride (7.8 g), triethylamine (5 ml) and acetic acid (50 ml) was heated at 120° C. for 18 hrs to give a dark brown-red solution. The solvent was evaporated under vacuum and the residue semi-purified by flash chromatography (silica. Acetic acid/ethanol/water mixtures). Final purification was by HPLC (RPC18. Water+0.1% TFA→MeCN+ 0.1% TFA gradient). UV/Vis (Water, 50: MeCN, 50: TFA, 0.1) 521 nm. $^1$H-nmr (DMSO) δ 1.68 (6H, s), 1.7-1.9 (4H, broad m), 2.60 (2H, t), 4.14 (2H, t), 6.36 (1H, t), 6.56 (1H, d), 7.21 (1H, m), 7.3-7.5 (5H, m), 7.65 (1H, m), 7.83 (1H, s), 8.39 (1H, t), 8.83 (1H, t) and 11.7 (1H, d). MS (MALDI-TOF) M+504.

13.4 2-{(1E,3E,5E)-5-[3-(5-Carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium 4-{2-[(1E,3E)-4-anilinobuta-1,3-dienyl]-3,3-dimethyl-5-sulfo-3H-indolium-1-yl}butane-1-sulfonate (250 mg) and 6-(2,3-dimethyl-5-sulfo-3H-indol-3-yl)hexanoic acid (312 mg) were mixed in pyridine (9 ml): acetic acid (9 ml): acetic anhydride (2 ml) and stirred at ambient temperature overnight. After evaporation of solvent under vacuum, the residue was then purified twice by preparative HPLC (RPC18. Water+0.1% TFA→MeCN+0.1% TFA gradient). The appropriate fractions were pooled and evaporated under vacuum. The residue was redissolved in water and freeze-dried to give the purified dye (135 mg). Observed pKa in aqueous phosphate buffers (via fluorescence): 7.0. UV/Vis (Water+0.1% TFA): 645 nm (ε=2.0×10$^5$ l mol$^{-1}$ cm$^{-1}$). MS (MALDI-TOF) MH+751. $^1$H-nmr (D$_2$O) δ 0.5-0.65 (1H, broad), 0.75-0.9 (1H, broad), 1.1 92H, m), 1.35 (2H, m), 1.5 (3H, s), 1.65 (6H, 2×s), 1.75-2.05 (6H, m), 2.1 (2H, t), 2.95 (2H, t), 4.05 (2H, broad t), 6.0 (1H, d), 6.2 (1H, d), 6.5 (1H, t), 7.2 (1H, d), 7.3 (1H, d) and 7.1-8.1 (6H, m).

13.5 2-{(1E,3E,5E)-5-[3-(5-Carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium, N-hydroxysuccinimidyl ester

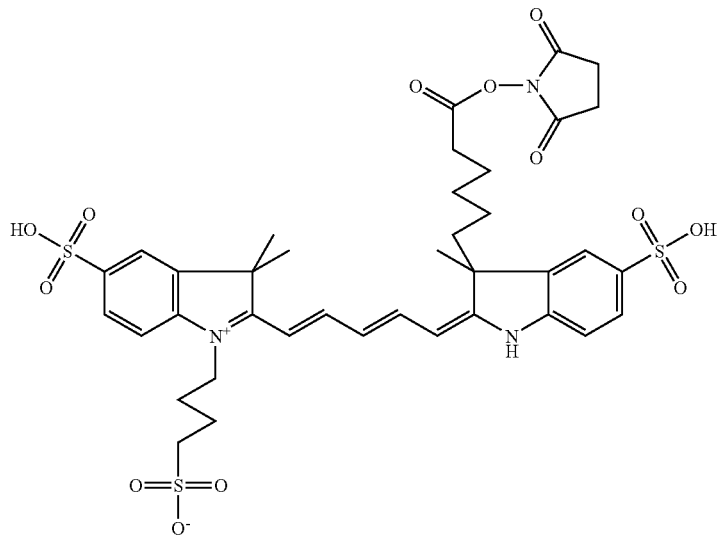

Carboxy dye (30 mg) was dissolved in anhydrous DMF (300 μl); to this were added O-(N-succinimidyl)-N,N,N',N'-tetramethyleneuronium hexafluorophosphate (HSPyU, 60 mg) and diisopropylethylamine (42 μl). The resulting solution was mixed for 2 hrs, whereupon TLC (RPC18. Water/MeCN/AcOH) revealed complete reaction. The reaction mix was evaporated under vacuum and the residue was purified by preparative HPLC (Water+0.1% AcOH→MeCN+0.1% AcOH gradient). Fractions containing the principal dye peak were pooled and evaporated under vacuum; the residue was redissolved in water and freeze-dried. UV/Vis (Water, 50: MeCN, 50: TFA, 0.1) 646 nm. MS (MALDI-TOF) MH+~850.

14. Synthesis and activation of 3-(5-carboxypentyl)-2-[(1E,3E,5E5-(5,7-dichloro-3,3-dimethyl-1,3-dihydro-2H-indol-2-ylidene)penta-1,3-dienyl]-3-methyl-5-sulfo-1-(4-sulfobutyl)-3H-indolium

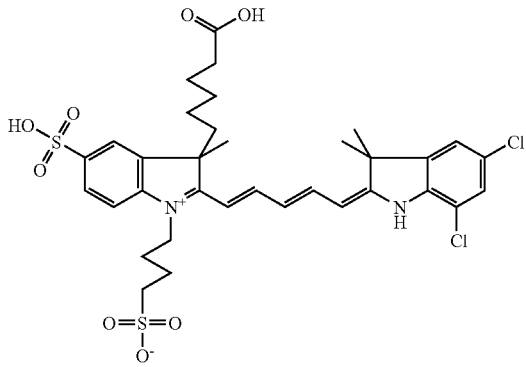

14.1 4-[3-(5-Carboxypentyl)-2,3-dimethyl-5-sulfo-3H-indolium-1-yl]butane-1-sulfonate 6-(2,3-Dimethyl-5-sulfo-3H-indol-3-yl)hexanoic acid (340 mg) and sodium acetate (100 mg) were dissolved in methanol (5 ml), then the solvent was evaporated under vacuum. The residue was treated with 1,4-butanesultone (680 mg) and 1,2-dichlorobenzene (5 ml); this mixture was heated at 150° C. for 18 hrs under nitrogen. A further aliquot of 1,4-butanesultone (500 mg) was added and heating continued for 4 hrs. After cooling, the solid product was collected by vacuum filtration, washed with dichlorobenzene and diethyl ether and dried. Crude yield 557 mg. After purification by preparative HPLC (RPC18. Water+0.1% TFA→MeCN+ 0.1% TFA gradient), the desired product was isolated. $^1$H-nmr (DMSO) δ 0.6-0.8 (2H, m), 1.05-1.12 (2H, m), 1.43 (2H, app. quin), 1.64 (3H, s), 1.95 (2H, aqq. quin), 2.05-2.42 (4H, m+2H, t), 3.01 (2H, t), 4.60 (2H, t), 7.97 (1H, d), 8.09 (1H, dd) and 8.13 (1H, d). LCMS: MH+476.

14.2 4-{2-[(1E,3E)-4-Anilinobuta-1,3-dienyl]-3-(5-carboxypentyl)-3-methyl-5-sulfo-3H-indolium-1-yl}butane-1-sulfonate 4-[3-(5-Carboxypentyl)-2,3-dimethyl-5-sulfo-3H-indolium-1-yl]butane-1-sulfonate (410 mg), malonaldehyde bis(phenylimine) monohydrochloride (500 mg), triethylamine (0.3 ml) and acetic acid (3 ml) were heated at 120° C. for 18 hrs to give a dark brown-red solution. The solvent was evaporated under vacuum and the residue semi-purified by HPLC (RPC18. Water+0.1% TFA→MeCN+0.1% TFA gradient). The product was then used directly. UV/Vis (Water, 50: MeCN, 50: TFA, 0.1) 523 nm. MS (MALDI-TOF) MH+605.

14.3 5,7-Dichloro-2,3,3-trimethyl-3H-indole 2,4-Dichlorophenylhydrazine.HCl (3.0 g), 3-methyl-2-butanone (3.0 ml) and acetic acid (25 ml) were mixed and heated at 120° C. for 3 hrs. A dark orange solution resulted. The solvent was evaporated under vacuum; the residue was partitioned between ethyl acetate and aqueous sodium hydrogen carbonate solution. The organic phase was collected, dried (MgSO$_4$), filtered and the solvent evaporated to give a dark oil. Purification by flash chromatography (silica: ethyl acetate/hexane) gave the product as a light orange oil, which solidified on standing. $^1$H-nmr (CDCl$_3$) δ 1.31 (6H, s), 2.32 (3H, s), 7.15 (1H, d), 7.26 (1H, s) and 7.32 (1H, d).

14.4 3-(5-carboxypentyl)-2-[(1E,3E,5E)-5-(5,7-dichloro-3,3-dimethyl-1,3-dihydro-2H-indol-2-ylidene)penta-1,3-dienyl]-3-methyl-5-sulfo-1-(4-sulfobutyl)-3H-indolium 4-{2-[(1E,3E)$_4$-Anilinobuta-1,3-dienyl]-3-(5-carboxypentyl)-3-methyl-5-sulfo-3H-indolium-1-yl}butane-1-sulfonate (250 mg) and 5,7-dichloro-2,3,3-trimethyl-3H-indole (230 mg) were mixed with acetic anhydride (1.0 ml) and DMF (10.0 ml). The mixture was stirred under nitrogen for 18 hrs, then at 50° C. for 24 hrs. The solvent was then evaporated under vacuum; the residue triturated with ether, dried and purified by preparative HPLC (RPC18. Water+0.1% TFA→MeCN+0.1% TFA gradient). The appropriate fractions were pooled and evaporated under vacuum to give the product dye, 84 mg. Observed pKa in aqueous phosphate buffers (via fluorescence): 6.05 UV/Vis (Water, 50: MeCN, 50: TFA, 0.1) 646 nm. MS (MALDI-TOF) MH+740.

14.5 3-(5-carboxypentyl)-2-[(1E,3E,5E)-5-(5,7-dichloro-3,3-dimethyl-1,3-dihydro-2H-indol-2-ylidene)penta-1,3-dienyl]-3-methyl-5-sulfo-1-(4-sulfobutyl)-3H-indolium, N-hydroxysuccinimidyl ester Carboxy dye (24 mg) was dissolved in anhydrous DMF (2 ml) and evaporated under vacuum to ensure dryness. O-(N-Succinimidyl)-N,N,N',N'-tetramethyluronium tetrafluoroborate (TSTU, 30 mg) was added, along with diisopropylethylamine (25 µl) and DMF (2 ml). The red solution was allowed to stand for 1 hr, whereupon TLC (RPC18. Water/MeCN/AcOH) revealed complete reaction. The reaction was quenched by addition of acetic acid (50 µl) and the solvent evaporated under vacuum. The residue was purified by preparative HPLC (Water+0.1% AcOH→MeCN+0.1% AcOH gradient). Fractions containing the principal dye peak were pooled and evaporated under vacuum; the residue was redissolved in water and freeze-dried. UV/Vis (Water, 50: MeCN, 50: TFA, 0.1) 646 nm. MS (MALDI-TOF) MH+837.

15. Synthesis and activation of 2-{(1E,3E,5E)-5-[3-(5-carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium

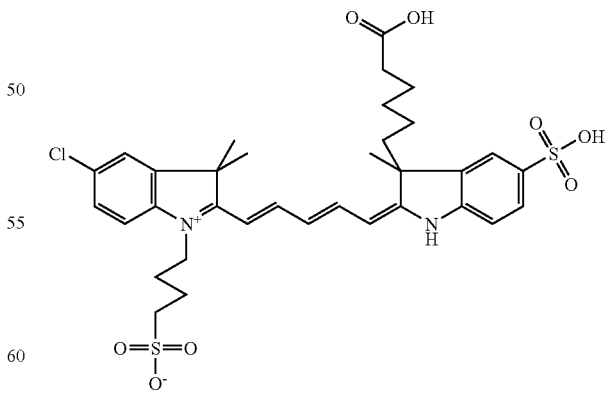

15.1 5-Chloro-2,3,3-trimethyl-3H-indole

4-Chlorophenylhydrazine.HCl (5.4 g), 3-methyl-2-butanone (6.4 ml) and acetic acid (70 ml) were mixed and heated to 80° C. initially, to give a solution. The temperature was then raised to 120° C. over 2 hrs, during which time a solid separated. TLC analysis (RPC18. Water/MeCN/TFA) indicated consumption of the hydrazine starting material and generation of a single main product. After evaporation of the solvent under vacuum, the residue was partitioned between ethyl acetate and aqueous sodium hydrogen carbonate solution. The organic phase was collected, dried (MgSO$_4$), filtered and the solvent evaporated to give the crude indolenine. Purification by flash chromatography (silica. Ethyl acetate/hexane) gave 4.66 g (80%) of pure product. MS (MALDI-TOF) M+193,195. $^1$H-nmr (CDCl$_3$) δ 1.30 (6H, s), 2.27 (3H, s), 7.23-7.29 (2H, m) and 7.44 (1H, d).
M

15.2 4-(5-Chloro-2,3,3-trimethyl-5-sulfo-3H-indolium-1-yl)butane-1-sulfonate 5-Chloro-2,3,3-trimethyl-3H-indole (1.94 g) and 1,4-butanesultone (5.0 g) were mixed in 1,2-dichlorobenzene (15 ml). The resulting solution was heated under nitrogen to 140° C. for 18 hrs, during which time a solid separated. After cooling to ambient temperature, this solid was collected by filtration, washed with dichlorobenzene followed by excess diethyl ether and then dried under vacuum to give the desired product. Yield 2.85 g (86%). MS (MALDI-TOF) MH+330, 332.

$^1$H-nmr (CD$_3$OD) δ 1.61 (6H, s), 1.95-1.98 (2H, m), 2.08-2.18 (2H, m), 2.88 (2H, t), 4.53 (2H, t), 7.65 (1H, dd), 7.86 (1H, d) and 7.93 (1H, d)

15.3 4-{2-[(1E,3E)-4-Anilinobuta-1,3-dienyl]-5-chloro-3,3-methyl-3H-indolium-1-yl}butane-1-sulfonate 4-(5-Chloro-2,3,3-trimethyl-5-sulfo-3H-indolium-1-yl)butane-1-sulfonate (0.99 g), malonaldehyde bis(phenylimine).HCl (1.55 g), triethylamine (1.0 ml) and acetic acid (10.0 ml) were mixed and heated at 120° C. for 18 hrs to give a dark purple solution. After evaporation of solvent, the crude reaction product was purified by flash chromatography (silica: MeOH/DCM) to give 1.12 g of pure product. UV/Vis (EtOH): 525 nm. MS (MALDI-TOF) M+458, 460.

15.4 2-{(1E,3E,5E-5-[3-(5-Carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium 4-{2-[(1E,3E)-4-Anilinobuta-1,3-dienyl]-5-chloro-3,3-dimethyl-3H-indolium-1-yl}butane-1-sulfonate (50 mg), 6-(2,3-dimethyl-5-sulfo-3H-indol-3-yl)hexanoic acid (50 mg), pyridine (2.25 ml), acetic acid (2.25 ml) and acetic anhydride (0.50 ml) were mixed and incubated at 90° C. for 1 hr, giving a deep blue solution. The solvent was then evaporated under vacuum and the residue triturated with diethyl ether. Purification by preparative HPLC (RPC18. Water/MeCN/TFA) yielded two blue components, the first-eluting component having the desired molecular mass and pH-sensitivity. Fractions containing this component were pooled and evaporated under vacuum to give the product dye, 16 mg. Observed pKa in aqueous phosphate buffers (via fluorescence): 7.44. UV/Vis (Water, 50: MeCN, 50: TFA, 0.1) 645 nm. MS (MALDI-TOF) M+704, 706.

15.5 2-{(1E,3E,5E)-5-[3-(5-carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium, N-hydroxysuccinimidyl ester

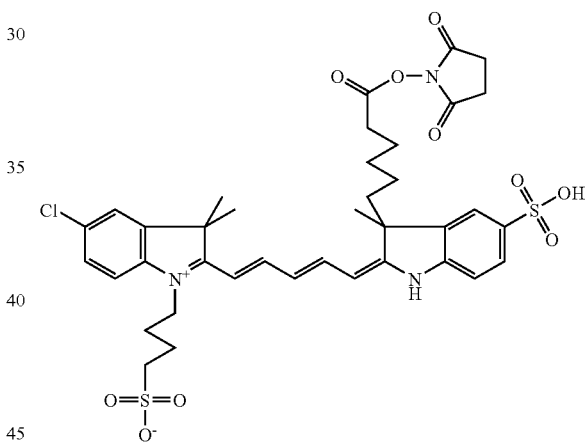

The carboxy dye (13.5 mg) was dissolved in anhydrous DMF (2 ml) and evaporated under vacuum to ensure dryness. O-(N-Succinimidyl)-N,N,N',N'-tetramethyluronium tetrafluoroborate (TSTU, 30 mg) was added, together with diisopropylethylamine (25 µl) and DMF (2 ml). The orange solution was allowed to stand for 1 hr, whereupon TLC (RPC18. Water/MeCN/AcOH) revealed complete reaction. The reaction was quenched by addition of acetic acid (50 µl) and the solvent evaporated under vacuum. The residue was purified by preparative HPLC (Water+0.1% AcOH→MeCN+0.1% AcOH gradient). Fractions containing the principal dye peak were pooled and evaporated under vacuum; the residue was redissolved in water and freeze-dried. UV/Vis (Water, 50: MeCN, 50: TFA, 0.1) 645 nm. MS (MALDI-TOF) M+801, 803.

16. Synthesis and activation of 3-(5-carboxypentyl)-2-[(1E,3E,5E)-5-(7-chloro-3,3-dimethyl-5-sulfo-1,3-dihydro-2H-indol-2-ylidene)penta-1,3-dienyl]-3-methyl-5-sulfo-1-(4-sulfobutyl)-3H-indolium

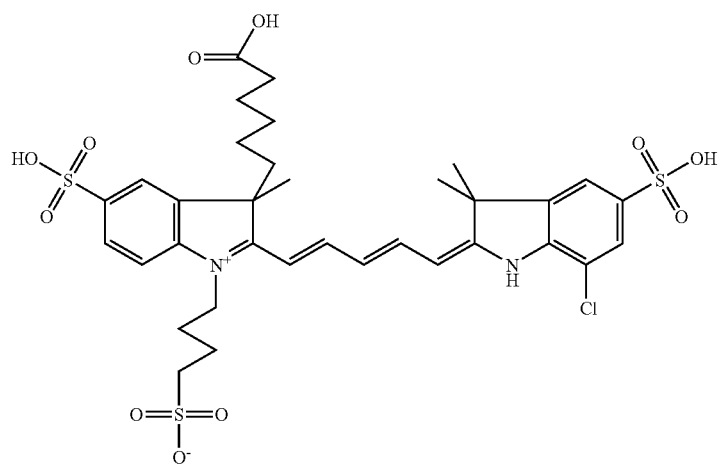

16.1 7-Chloro-2,3,3-trimethyl-3H-indole-5-sulfonic acid

2-Chloroaniline-4-sulfonic acid (2.5 g, 9.2 mmol) was dissolved in HCl (conc.; 40 ml) and cooled to 0° C. A solution of sodium nitrite (1.26 g, 18.3 mmol) in H$_2$O (10 ml) was transferred to a dropping funnel and added dropwise to the reaction vessel over 2 h. After stirring for 2 h at 0° C., stannous chloride (8.3 g, 36.9 mmol; dissolved in 10 ml conc. HCl) was added dropwise over 2 h. The reaction mixture was then allowed to warm to room temperature and stirred overnight. The reaction mixture was then filtered and the filtrate discarded. The isolated solid was then transferred to a round-bottomed flask and treated with acetic acid (15 ml), potassium acetate (3 g) and 3-methyl-2-butanone (3 ml). After heating the vessel at 140° C. for 4 h, the reaction mixture was concentrated in vacuo and the resultant gum purified by RP-HPLC (Phenomenex Synergi; 10u hydro-RP 80, 250×21.20 mm; MeCN:H$_2$O; 0-100% MeCN 30 min; 10 ml/min, RT=14 min) to isolate the desired product (550 mg; 2 mmol, 22%). MS (MALDI-TOF) MH$^+$273.

16.2 3-(5-Carboxypentyl)-2-[(1E,3E,5E)-5-(7-chloro-3,3-dimethyl-5-sulfo-1,3-dihydro-2H-indol-2-ylidene)penta-1,3-dienyl]-3-methyl-5-sulfo-1-(4-sulfobutyl)-3H-indolium To a solution of 7-chloro-2,3,3-trimethyl-3H-indole-5-sulfonic acid (50 mg; 0.18 mmol) in acetic acid/pyridine/acetic anhydride (4.5:4.5:1; 10 ml) was added (2E)-3-(5-carboxypentyl)-7-chloro-3-methyl-1-pentyl-2-[(2E,4E)-4-(phenylimino)but-2-enylidene]indoline-5-sulfonate (110 mg; 0.18 mmol). The reaction mixture was heated at 60° C. for 4 h then concentrated in vacuo to yield the crude dye. The resultant gum was purified by prep RP-HPLC (Phenomenex Synergi; 10 u hydro-RP 80, 250×21.20 mm; MeCN:H$_2$O; 0-100% MeCN 30 min; 10 ml/min, R=16 min) to yield the desired product (10 mg; 0.01 mmol; 7%). MS (MALDI-TOF) MH$^+$783

16.3 3-(5-Carboxypentyl)-2-[(1E,3E,5E)-5-(7-chloro-3,3-dimethyl-5-sulfo-1,3-dihydro-2H-indol-2-ylidene)penta-1,3-dienyl]-3-methyl-5-sulfo-1-(4-sulfobutyl)-3H-indolium, N-hydroxysuccinimidyl ester

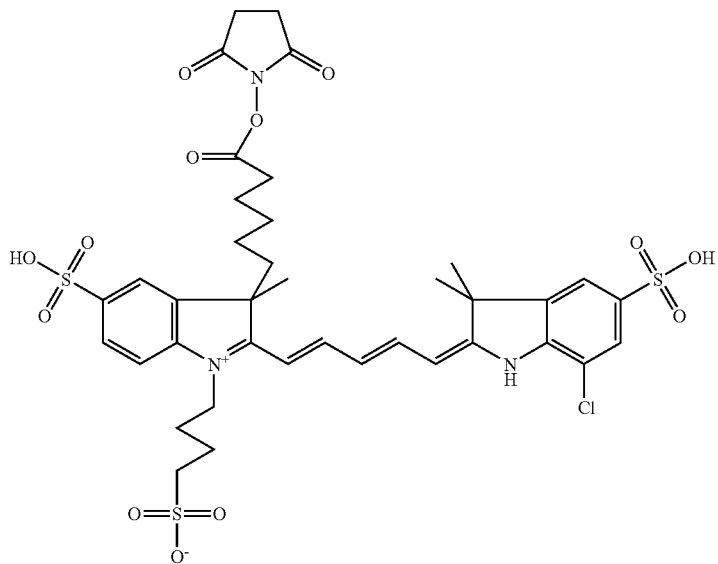

To a stirred solution of 6-[(2E)-2-[(2E,4E)-5-(7-chloro-3,3-dimethyl-5-sulfo-3H-indol-2-yl)penta-2,4-dienylidene]-3-methyl-5-sulfo-1-(4-sulfobutyl)-2,3-dihydro-1H-indol-3-yl] hexanoic acid (9 mg; 0.01 mmol) in DMF (3 ml) was added DIPEA (2 ml) followed by O-(N-succinimidyl-N,N,N',N'-bis-tetramethylene)uronium hexafluorophosphate (14 mg; 0.05 mmol). After 4 h, the reaction mixture was concentrated in vacuo and the resultant gum purified by RP-HPLC (Phenomenex Synergi; 10u hydro-RP 80, 250×21.20 mm; MeCN:H$_2$O; 0-100% MeCN 30 min; 10 ml/min, RT=17 min) to isolate the product (6 mg; 0.007 mmol; 53%). Observed pKa in aqueous phosphate buffers (via fluorescence): 6.2. MS (MALDI-TOF) M+Na$^+$902

17. Synthesis of 3-(5-carboxypentyl)-3-methyl-2-{(1E,3E,5E)-5-[3-methyl-5-sulfo-3-(4-sulfobutyl)-1,3-dihydro-2H-indol-2-ylidene]penta-1,3-dienyl}-5-sulfo-1-(4-sulfobutyl)-3H-indolium

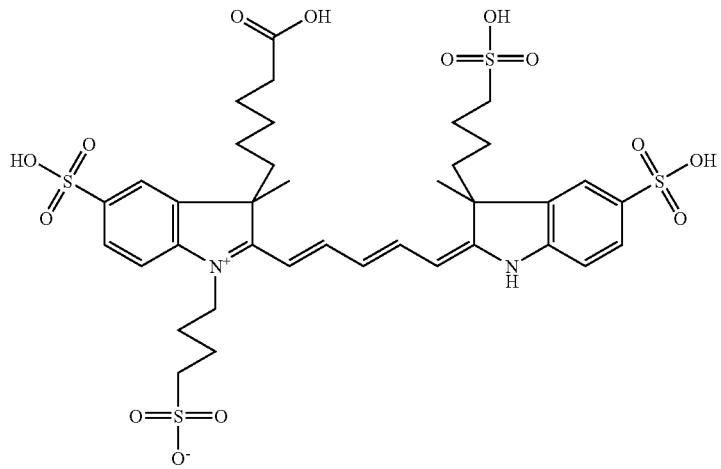

17.1 5-Methyl-6-oxoheptane-1-sulfonic acid

Ethyl 2-methylacetoacetate (43.2 g) in N,N-dimethylformamide (25 ml) was added to a suspension of sodium hydride (12.0 g of 60% NaH in mineral oil) in N,N-dimethylformamide (100 ml), dropwise with ice-bath cooling. This mixture was allowed to warm to ambient temperature for 30 mins before re-cooling. 1,4-butanesultone (40.8 g) in N,N-dimethylformamide (25 ml) was then added dropwise. The final mixture was heated at 50° C. for 18 hrs, then quenched with 50 ml of water. The solvent was evaporated under vacuum; the residue was partitioned between water and diethyl ether. The aqueous layer was collected, washed with fresh diethyl ether and evaporated under vacuum; final drying was under high vacuum over phosphorus pentoxide. A yield of 103 g of 5-(ethoxycarbonyl)-5-methyl-6-oxoheptane-1-sulfonic acid was obtained.

This intermediate was dissolved in concentrated hydrochloric acid (200 ml) and reacted at 90° C. for 3 hrs, then the solvent was evaporated under vacuum. The residue was purified by flash chromatography (silica. Dichloromethane→ethanol). Fractions containing the product were pooled and evaporated under vacuum to give the title compound, 49.6 g. $^1$H-nmr ($D_2O$) δ1.05 (3H, d), 1.3-1.8 (6H, m), 2.20 (3H, s), 2.65 (1H, m), and 2.90 (2H, m)

17.2 2,3-Dimethyl-3-(4-sulfobutyl)-3H-indole-5-sulfonic acid

4-Hydrazinobenzenesulfonic acid (1.88 g), 5-methyl-6-oxoheptanesulfonic acid (2.5 g) and acetic acid (50 ml) were mixed and heated under reflux for 6 hrs. The solvent was evaporated under vacuum, then the residue was triturated with 2-propanol to yield the crude product as a yellow solid. This was purified by HPLC as required ($RPC_{18}$. Water+0.1% TFA). $^1$H-nmr ($D_2O$) δ0.8-1.0 (2H, m), 1.55-1.65 (5H,=3H, s+2H, m), 2.16 (1H, ddd), 2.29 (1H, ddd), 2.75 (2H, m), 2.81 (partially d-exchanged methyl singlet), 7.71 (1H, d), 7.94 (1H, d) and 8.01 (1H, d). UV/Vis (Water+0.1% TFA): 269, 229 nm. MS (LCMS): MH$^+$362. Acc. Mass: Found, 362.0729. MH$^+$=$C_{14}H_{20}NO_6S_2$ requires 362.0732 (−0.8 ppm).

17.3 3-(5-Carboxypentyl)-3-methyl-2-{(1E,3E,5E)-5-[3-methyl-5-sulfo-3-(4-sulfobutyl)-1,3-dihydro-2H-indol-2-ylidene]penta-1,3-dienyl}-5-sulfo-1-(4-sulfobutyl)-3H-indolium 4-{2-[(1E,3E)-4-Anilinobuta-1,3-dienyl]-3-(5-carboxypentyl)-3-methyl-5-sulfo-3H-indolium-1-yl}butane-1-sulfonate (made as in Example 14.2, 50 mg) and 2,3-dimethyl-3-(4-sulfobutyl)-3H-indole-5-sulfonic acid (50 mg) were mixed in pyridine (2.25 ml), acetic acid (2.25 ml) and acetic anhydride (0.50 ml) and stirred at ambient temperature under nitrogen for 18 hrs, then for 2 hrs at 60° C. The resulting green-blue solution was evaporated under vacuum. The residue was purified by HPLC ($RPC_{18}$. Water/MeCN/TFA gradient). Fractions containing the principal dye peak were collected, pooled and evaporated under vacuum to give the title dye, 22 mg. UV/Vis (Water+0.1% TFA): 651 nm. MS (MALDI-TOF): M+872.

18. Synthesis of 6-[9-(5-carboxypentyl)-5,7-dimethyl-5,11-disulfo-1,2,9,14,15,16,15a,16a,2a-nonahydroindolo-[2'',1''-1',2']isoquinolino[7',6'-4,3]pyridino[1,2-a]indolin-7-yl]hexanoic acid (rigid Cy3)

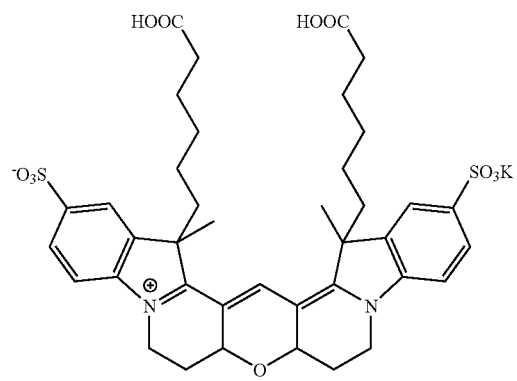

To a stirred solution of 6-(2,3-dimethyl-5-sulfo-3-hydroindol-3-yl)hexanoic acid (150 mg, 0.45 mmol) in ethanol (20 ml) at ambient temperature was added hydrobromic acid (3 ml, 40% aqueous solution). After 1 hr the reaction solvent was removed in vacuo. The hydrobromide salt was redissolved in acetonitrile (20 ml) and acetic acid (200 ml) and acrolein diethyl acetal (10 g, 75 mmol) was added. The reaction mixture was heated to 70° C. for 20 minutes. The solution was cooled and the solvent removed in vacuo. The product was rapidly purified on reverse phase C18 column using 1:1 water/acetonitrile (containing 0.1% TFA) as solvent. All fractions were monitored by RP C18 TLC. Fractions containing product were pooled. Evaporation of the solvent gave a sticky mass (120 mg, 36%). It was immediately used for the next reaction.

To a stirred solution of 6-[1-(3,3-diethoxypropyl)-2,3-dimethyl-5-sulfo-3-hydroindole-3 yl]hexanoic acid (100 mg, 0.21 mmol) in pyridine (5 ml) at 120° C. was added dropwise, triethyl orthoformate (100 mg, 67 mmol) over 30 minutes. After 2 hrs the reaction mixture was cooled. The product was purified by reversed phase C18 column using water-acetonitrile mixture (containing 0.1% TFA) as solvent. The product was obtained as a pink solid (45 mg, 40%); λmax: 560 nm water, λem 570 nm, φ0.09

To a stirred solution of 1,1-di-(3,3-diethoxypropyl)-3-methyl-3'(6-carboxypentenyl)-indocarbocyanine (40 mg, 0.04 mmol) in ice water was added 50% aqueous sulphuric acid (2 ml). The reaction mixture was heated at 40° C. for 30 minutes. The mixture was cooled and neutralized with triethylamine. Solvent was removed under vacuum on a flash evaporator was obtained as red solid. λmax 565 nm, λem 584 nm, φ0.8.

19. Synthesis of 6,7,9,10-tetrahydro-2,14-disulphonato-16,16,18-trimethyl-7aH,8aH-bisindolinium[3,2-a,3'2'-a]pyrano[3,2-c;5,6-c']dipyridin-5-ium-18-hexanoic acid

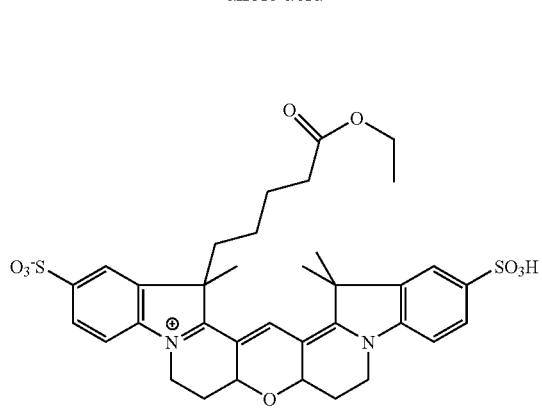

19.1 1-(3,3-Diethoxypropyl)-3-(6-ethoxy-6-oxohexyl)-2,3-dimethyl-3H-indolium-5-sulfonate

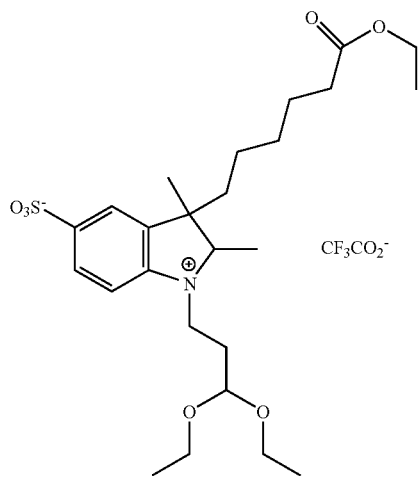

6-(2,3-Dimethyl-5-sulfo-3H-indol-3-yl)hexanoic acid was synthesised as described in Example 5. To a stirred solution of 6-(1-ethyl-2,3-dimethyl-5-sulfo-3H-indol-3-yl)hexanoic acid (1.8 g, 5.3 mmol) in ethanol (200 ml) at ambient temperature was added hydrobromic acid (10 ml 48% aqueous solution). After 1 Hr the reaction solvent was removed in vacuo. The hydrobromide salt was re-dissolved in acetonitrile (150 ml) and acetic acid (1.54 ml) and acrolein diethyl acetal (6.6 g, 51 mmol). The reaction mixture was heated to 70° C. for 30 minutes. The solution was cooled and the solvent removed in vacuum. The product was rapidly purified by preparative HPLC on reverse phase C18 column using gradient elution of water containing 10% acetonitrile to acetonitrile (containing 0.1% TFA) as solvent over 30 minutes. All fractions were monitored by MALDI-TOF mass spectrometry (M/Z=498). Fractions containing product mass were pooled. Evaporation of the solvent gave a sticky mass (162 mg 11%). It was immediately used for the next reaction.

19.2 1-(3,3-Diethoxypropyl)-2,3,3-trimethyl-3H-indolium-5-sulphonate

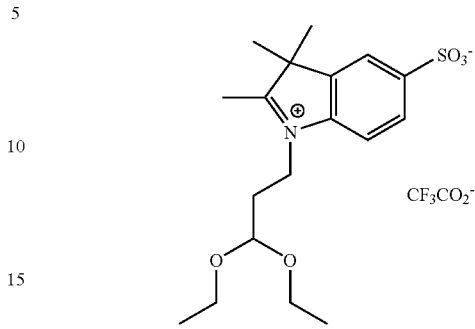

Potassium 2,3,3-trimethyl-3H-indole-5-sulfonate was synthesised following the procedure described in Mujumdar, R, B Bioconjugate Chem., (1993), 4(2), 105-111. To a stirred solution of potassium 2,3,3-trimethyl-3H-indole-5-sulfonate (5 g, 18 mmol) in ethanol (250 ml) at ambient temperature was added hydrobromic acid (50 ml 48% aqueous solution). After 1 Hr the reaction solvent was removed in vacuo. The hydrobromide salt was re-dissolved in acetonitrile (200 ml) and acetic acid (5 ml) and acrolein diethyl acetal (42.25 g, 325 mmol). The reaction mixture was heated to 70° C. for 60 minutes. The solution was cooled and the solvent removed in vacuum. The product was rapidly purified by preparative HPLC on reverse phase C18 column using gradient elution of water containing 10% acetonitrile to acetonitrile over 60 minutes (containing 0.1% TFA) as solvent. All fractions were monitored by MALDI-ToF mass spectrometry (M/Z 369). Fractions containing product mass were pooled. Evaporation of the solvent gave a sticky mass (1.8 g 36%). It was immediately used for the next reaction.

19.3 1-(3,3-diethoxypropyl)-2-{(1E,3E)-3-[1-(3,3diethoxypropyl)-3,3-dimethyl-5-sulfonato-1,3-dihydro-2H-indol-2-ylidene]prop-1 -enyl}-3-(6-ethoxy-6-oxohexyl)-3-methyl-3H-indolium-5-sulfonate

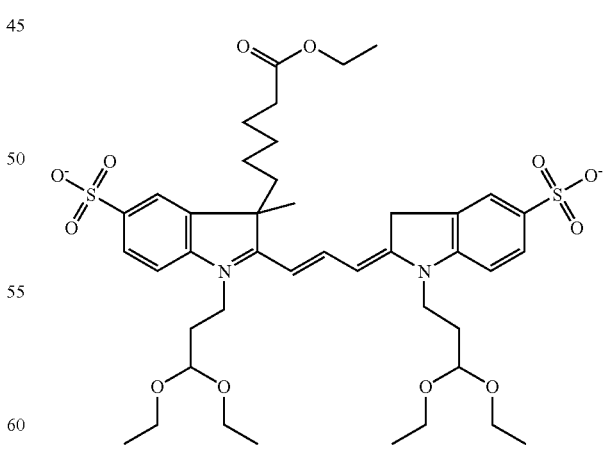

To 120 mg (0.325 mmol) of 1-(3,3-diethoxypropyl)-3-(6-ethoxy-6-oxohexyl)-2,3-dimethyl-3H-indolium-5-sulponate was added pyridine (5 ml) to dissolve. To 162 mg (0.325 mmol) 1-(3,3-diethoxypropyl)-2,3,3-trimethyl-3H-indolium-5-sulphonate was added pyridine (5 ml) to dissolve. The contents of the above flasks were combined, stirred and triethylorthoformate (385 mg, 2.6 mmol) added. The reaction mixture was heated to 120° C. for 5 Hr. The solution was cooled and the solvent removed in vacuum. The product was purified by preparative HPLC on reverse phase C18 column using gradient elution of water to acetonitrile over 90 minutes (containing 0.1% TFA) as solvent. All fractions were monitored by MALDI-TOF mass spectrometry (M/Z=1006). Fractions containing product mass were pooled. Evaporation of the solvent gave a pink solid (78 mg 13%). It was immediately used for the next reaction.

19.4 6,7,9,10-tetrahydro-2, 14-disulphonato-16,16, 18-trimethyl-7aH,8aH-bisindolinium[3,2-a,3'2'-a] pyrano[3,2-c;5,6-c']dipyridin-5-ium-18-hexanoic acid 78 mg (8.88×10$^{-5}$ mol) of 1-(3,3-diethoxypropyl)-2-{(1E, 3E)-3-[1-(3, 3-diethoxypropyl)-3,3-dimethyl-5-sulfonato-1, 3-dihydro-2H-indol-2-ylidene]prop-1-enyl}-3-(6-ethoxy-6-oxohexyl)-3-methyl-3H-indolium-5-sulfonate was dissolved in sulphuric acid (2 ml 48% aqueous solution) and stirred at ambient temperature for 4 hours. The solvent was removed under vacuum. The product was purified by preparative HPLC on reverse phase C18 column using gradient elution over 90 minutes of water to acetonitrile (containing 0.1% TFA) as solvent. All fractions were monitored by MALDI-TOF mass spectrometry. Fractions containing the product mass were pooled. Evaporation of the solvent gave a pink solid (27 mg 35%).

20. General Protein Labeling Procedure

The following protein labeling procedure was followed to label sheep IgG with NHS ester of Cy3.10, Cy3.24, NSCy3, Cy7.18 and NSCy7. Stock solutions of the succinimidyl active esters were made in dry DMF (0.3-1.0 mg active ester/100 μL) and are stable for days when stored at 4° C. The active esters are also stable in distilled water for several hours provided the pH of the solution is not basic. Aqueous solutions of the dyes can be used for labeling antibodies if the use of DMF is not suitable for certain antibodies. The concentration of cyanine fluorophore in the stock solution was determined by measuring the absorbance of an aliquot of the appropriately diluted stock solution in phosphate-buffered saline (PBS) and using the extinction coefficient of the dye. The stock solution concentration of cyanine fluorophore in the active ester form was then determined by reverse-phase HPLC (typically 50-95% but sometimes as low as 35%). The antibody labeling was carried out in 0.1M carbonate-bicarbonate buffer (pH 9.4) for 15 minutes at room temperature. The sheep IgG (1 mg, 6.45 mM) was dissolved in 0.25-1 mL buffer solution and the desired amount of dye (e.g., 20 μL of stock containing 0.35 mg active ester/100 μL DMF) was added during vigorous vortex mixing. Unconjugated dye was separated from the labeled protein by gel permeation chromatography (0.7×20 cm column of Sephadex G-50) using pH 7 buffer solution as eluent.

21. Determination of Dye-to-Antibody Ratio

A simple method for estimating dye/protein (d/p) ratios involves direct measurement of the protein absorbance at 280 nm and dye absorbance at the absorption maximum. Specifically, the dye/protein ratio is calculated using the equation below with measured values of the absorbance of the labeled dye (Cy3 at 550 nm or Cy7 at 750 nm) and the absorbance of protein at 280 nm. The extinction coefficients of Cy3 and Cy7 are approximately 150,000 and 250,000 respectively. The extinction coefficient of the IgG antibody at 280 nm was taken to be 170,000 L/mol-cm. The factor "X" in the denominator accounts for dye absorption at 280 nm which is 0.05 (for both Cy3) and 0.08 (for Cy7) of the absorption of the dye at its maximum absorption ($A_{dye}$).

$$\frac{D}{P} = \frac{A_{dye} * E_{prot}}{(A_{280} - 0.05 A_{dye}) * E_{dye}}$$

A more accurate method is needed when the labeling reagent shows significant spectral changes when bound to the antibody molecule. For example, this approach is needed when both dimers and monomers of dye, which have different absorption peaks and different extinction coefficients, are present on the protein at higher d/p ratios. In this case, the labeled protein is dissolved in formamide for absorption spectroscopy and the extinction coefficients of the dye determined independently for the calculation

22. Measurement of pKa Values of pH-Sensitive Cyanine Dyes

The general method of pKa determination was performed as follows. Purified dye was dissolved in water to give a bulk stock solution (if necessary, a limited amount of acetonitrile was added to ensure solubility). By experiment, the volume of this stock solution that was required to be added to 10.0 ml of water+0.1% v/v trifluoroacetic acid, in order to give an absorbance of 0.5±0.02 at the dye peak wavelength, was determined. This volume of bulk stock solution was then added to 10.0 ml of water, to be used as the working stock solution.

Aqueous phosphate buffers were prepared covering the region of pH 4-9 {see "Data for Biochemical Research", p. 432, 3$^{rd}$ edition, R. M. C Dawson, D. C. Elliott, W. H. Elliott & K. M. Jones, 1987 Oxford University Press. Buffers outside the listed range were made by adding in orthophosphoric acid or sodium hydroxide}. Plastic fluorescence cuvettes were then charged with 3.5 ml of each buffer. A fixed volume of dye working stock solution (in the range 50-250 μl) was added to a cuvette of buffer, the solution mixed and the fluorescence signal measured immediately {Perkin Elmer LS55 fluorimeter, excitation 640 nm. Emission spectrum was scanned and fluorescence intensity value at 680 nm recorded}. This was repeated for all cuvettes. The graph of fluorescence intensity versus pH was plotted using PRISM, the data fitted to a sigmoidal dose-response curve and the pKa value extracted as the calculated IC50 value from the fitting.

Table 1 lists the pKa values of the carboxy dyes prepared in the above four examples, along with a selection of non-functional dyes (dyes 5-9) that were prepared using the same methodology. These extra examples help to explain the effect of substitution on the observed pKa value of the dye chromophore, and show that this figure can be tuned to any value across the physiological pH range.

TABLE 1

| No | Name | Structure | pKa |
|---|---|---|---|
| 1 | 2-{(1E,3E,5E)-5-[3-(5-carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium | 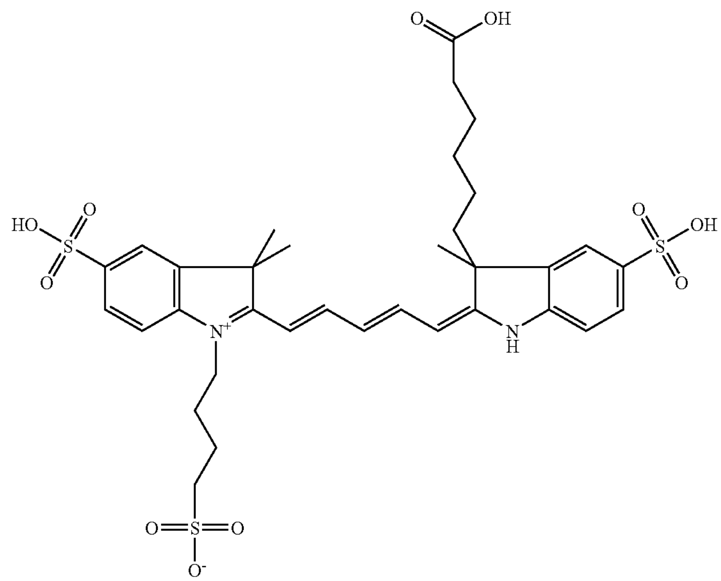 | 7.0 |
| 2 | 3-(5-carboxypentyl)-2-[(1E,3E,5E)-5-(5,7-dichloro-3,3-dimethyl-1,3-dihydro-2H-indol-2-ylidene)penta-1,3-dienyl]-3-methyl-5-sulfo-1-(4-sulfobutyl)-3H-indolium | 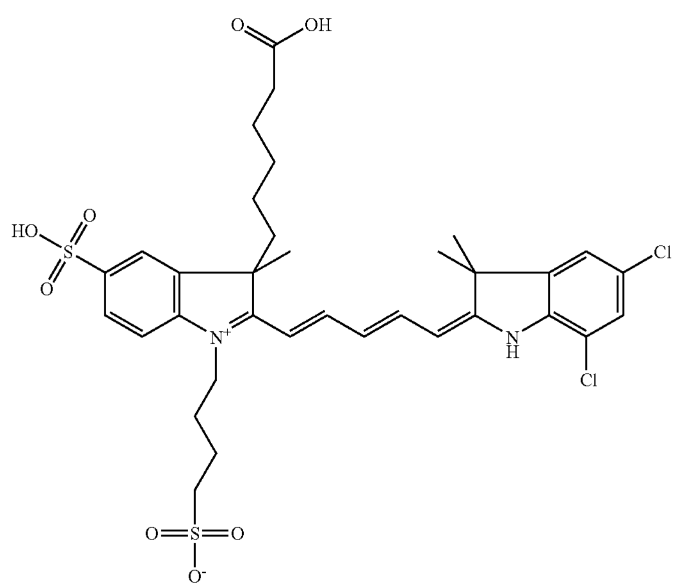 | 6.05 |

TABLE 1-continued

| No | Name | Structure | pKa |
|----|------|-----------|-----|
| 3 | 2-{(1E,3E,5E)-5-[-(5-carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium | 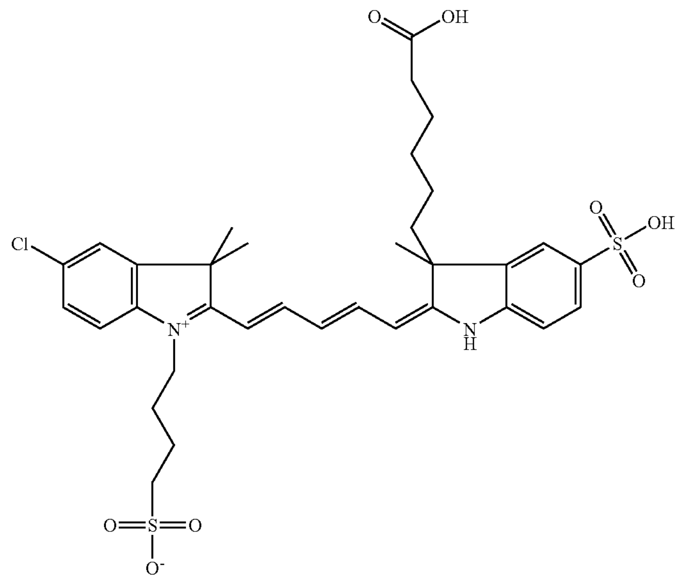 | 7.44 |
| 4 | 3-(5-carboxypentyl)-2-[(1E,3E,5E)-5-(7-chloro-3,3-dimethyl-5-sulfo-1,3-dihydro-2H-indol-2-ylidene)penta-1,3-dienyl]-3-methyl-5-sulfo-1-(4-sulfobutyl)-3H-indolium | 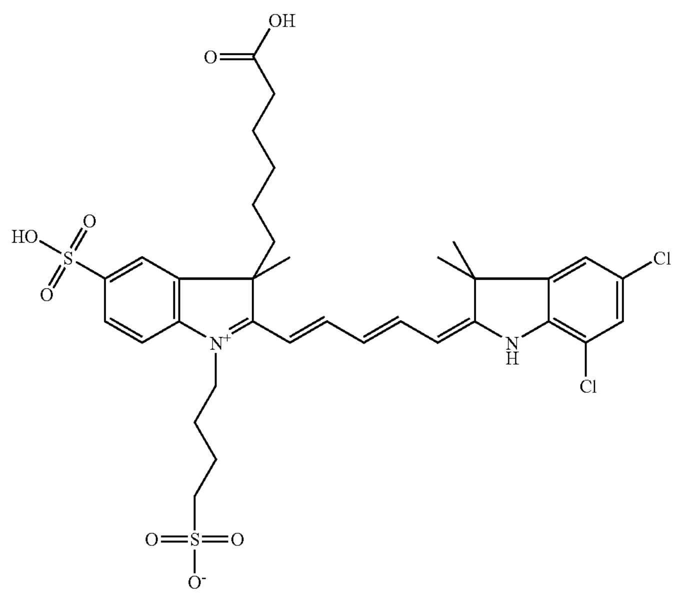 | 6.2 |
| 5 | 2-[(1E,3E,5E)-5-(3,3-dimethyl-1,3-dihydro-2H-indol-2-ylidene)penta-1,3-dienyl]-3,3-dimethyl-5-sulfo-1-(4-sulfobutyl)-3H-indolium | 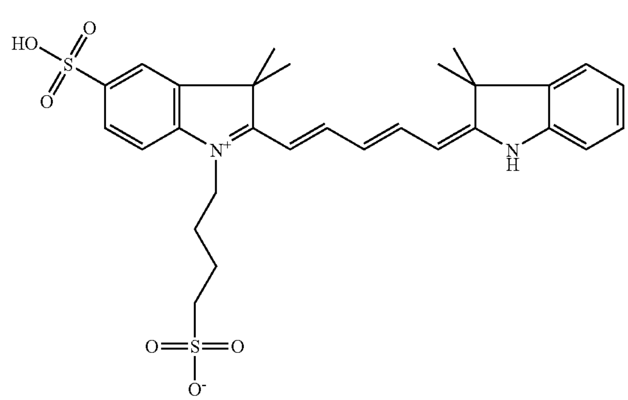 | 7.0 |

TABLE 1-continued

| No | Name | Structure | pKa |
|---|---|---|---|
| 6 | 2-[(1E,3E,5E)-5-(3,3-dimethyl-5-sulfo-1,3-dihydro-2H-indol-2-ylidene)penta-1,3-dienyl]-3,3-dimethyl-5-sulfo-1-(4-sulfobutyl)-3H-indolium | 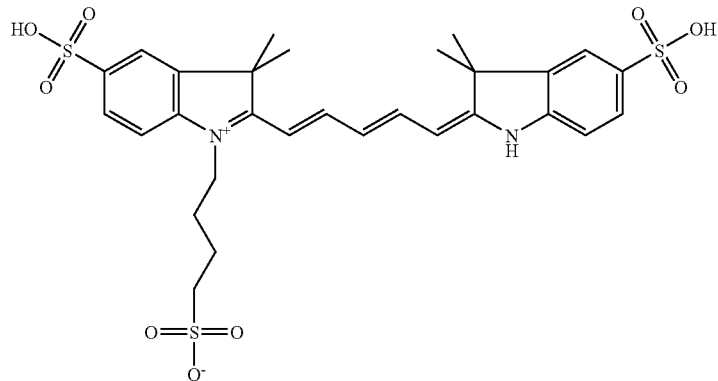 | 7.0 |
| 7 | 2-[(1E,3E,5E)-5-(5-chloro-3,3-dimethyl-1,3-dihydro-2H-indol-2-ylidene)penta-1,3-dienyl]-3,3-dimethyl-5-sulfo-1-(4-sulfobutyl)-3H-indolium | 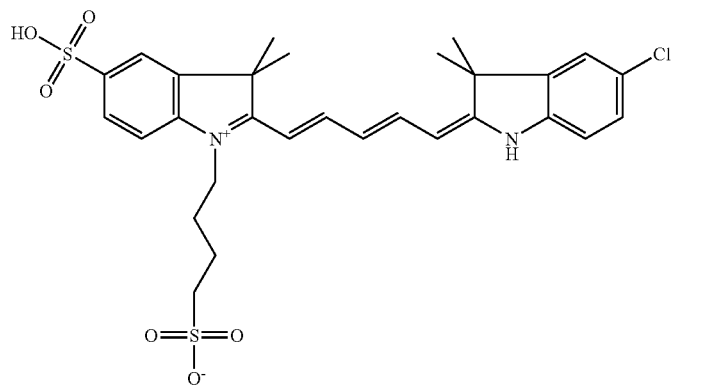 | 6.65 |
| 8 | 2-[(1E,3E,5E)-5-(5-cyano-3,3-dimethyl-1,3-dihydro-2H-indol-2-ylidene)penta-1,3-dienyl]-3,3-dimethyl-5-sulfo-1-(4-sulfobutyl)-3H-indolium | 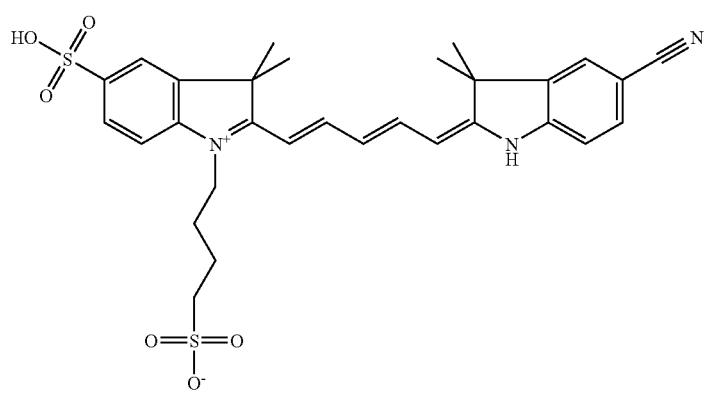 | 6.65 |
| 9 | 5-chloro-2-[(1E,3E,5E)-5-(3,3-dimethyl-5-sulfo-1,3-dihydro-2H-indol-2-ylidene)penta-1,3-dienyl]-3,3-dimethyl-1-(4-sulfobutyl)-3H-indolium | 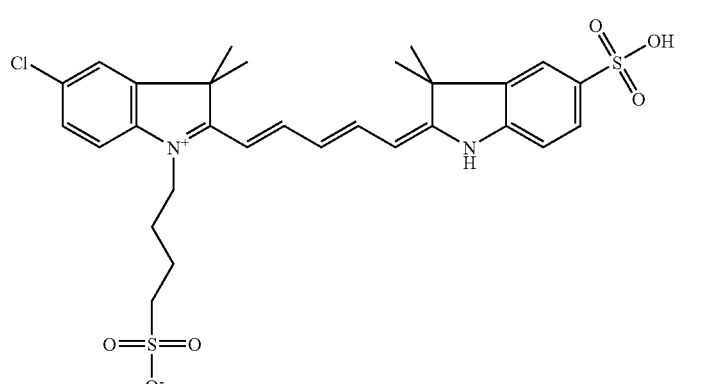 | 7.36 |

Comparison of dyes 5 and 6 show that substitution of H for sulfonate, in the position para- to the unquaternized nitrogen, has no measureable effect on dye pKa. Furthermore, dye 1 shows that addition of the functional arm onto dye 6 has no measurable effect on dye pKa.

Comparison of the above dye set with dyes 7, 4 and 2 shows the effect of incorporating an electron-withdrawing group, such as Cl, onto the unquaternized indolenine unit. Substitution of Cl para- to the unquaternized nitrogen lowers the dye pKa by 0.3-0.4 units (dye 1→dye 7). Substitution of Cl ortho- to the unquaternized nitrogen lowers the dye pKa by ~0.8 units (dye 1→dye 4). Incorporating both substitutions gives an additive effect, lowering the pKa by ~1.0 unit (dye 1→dye 2). Dye 8 shows that another electron-withdrawing group, cyano, has a similar effect to chloro. Fluoro and trifluoromethyl act similarly.

Comparison of dyes 9 and 3 with dyes 6, 7 and 1 shows the effect of incorporating an electron-withdrawing group, such as Cl, onto the quaternized indolenine unit. Substitution of Cl para- to the quaternized nitrogen raises the dye pKa by 0.3-0.4 units. Hence the pKa of these pH-sensitive dyes can be adjusted from that of the base structures, at pKa=7.0, in either direction by the considered placement of electron-withdrawing groups such as chloro (fluoro, cyano, trifluoromethyl).

The contents of references cited herein are incorporated herein by reference in their entirety.

We claim:

1. A compound of the following general formula (XIII)

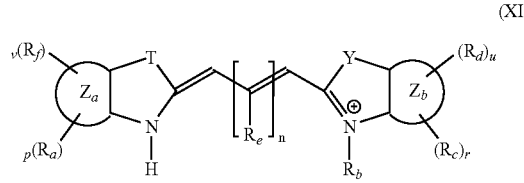

wherein $R_a$, $R_c$, $R_d$ and $R_f$ are independently selected from hydrogen, halogen and $-SO_3^-$;

$R_b$ is selected from V or L-V, where L is a bond or $C_{1-22}$ straight or branched alkyl, optionally containing 0, 1 or 2 unsaturations or unsaturated pendent or interchain groups selected from alkenyl, alkynyl and aryl groups; and V is selected from hydrogen, $-SO_3^-$, $-COOH$ and a reactive group;

$R_e$ is hydrogen;

T is

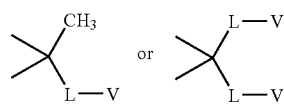

wherein each L and V are independently as defined above;

Y is selected from the group consisting of O, S, $-CH=CH-$, $>C(CH_3)_2$, and

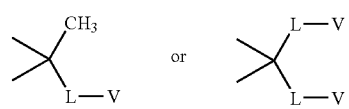

wherein each L and V are independently as defined above; $Z_a$ and $Z_b$ are, independently, fused

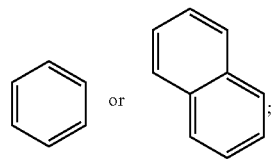

n is an integer from 1-4; and p, u, v and r are independently an integer from 0-4, wherein at least one group -L-V in groups T and/or Y is a substituted alkyl group.

2. A compound of the following general formula (XIII)

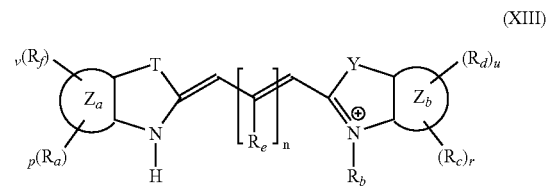

wherein $R_a$, $R_c$, $R_d$ and $R_f$ are independently selected from hydrogen, halogen and $-SO_3^-$;

$R_b$ is selected from V or L-V, where L is a bond or $C_{1-22}$ straight or branched alkyl, optionally containing 0, 1 or 2 unsaturations or unsaturated pendent or interchain groups selected from alkenyl, alkynyl and aryl groups; and V is selected from hydrogen, $-SO_3^-$, $-COOH$ and a reactive group;

$R_e$ is hydrogen;

T is

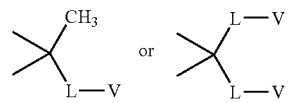

wherein each L and V are independently as defined above;

Y is selected from the group consisting of O, S, $-CH=CH-$, $<C(CH_3)_2$, and

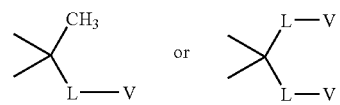

wherein each L and V are independently as defined above; $Z_a$ and $Z_b$ are, independently, fused

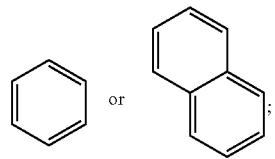

n is an integer from 1-4; and p, u, v and r are independently an integer from 0-4, wherein said at least one group -L-V in groups T and/or Y is selected from a carboxyalkyl group, a sulfoalkyl group and a reactive group.

3. A compound of claim 1 or claim 2 wherein said reactive group is selected from:

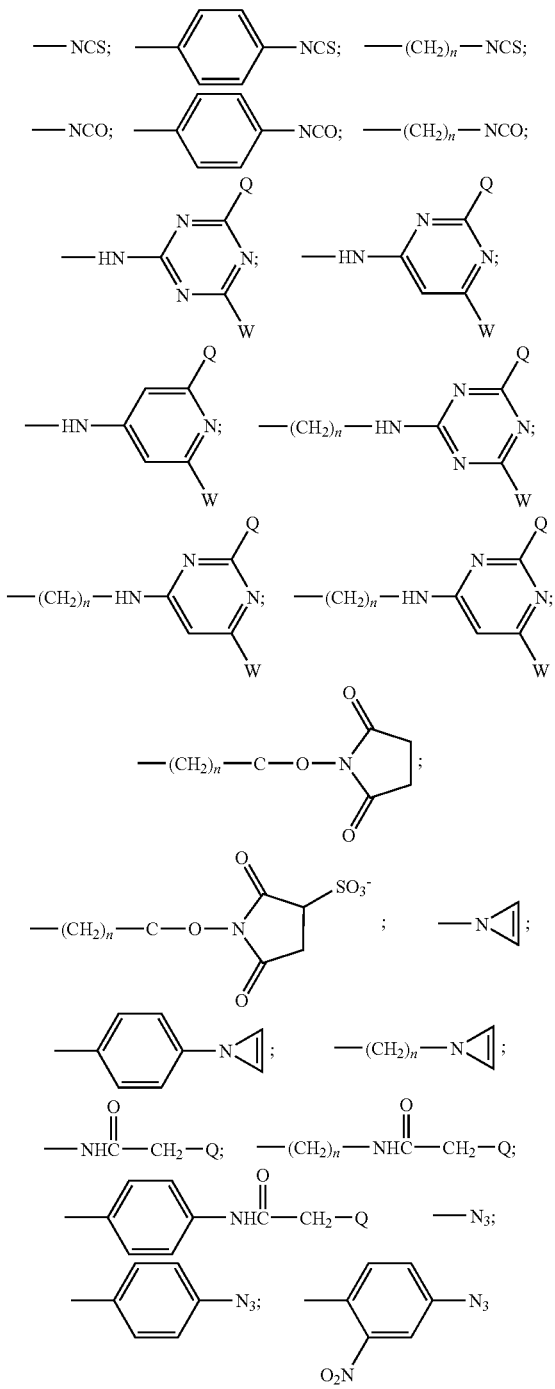

where n is an integer of 1-10, and Q and W are leaving groups.

4. A method for detecting acidic or basic conditions comprising contacting a compound according to claim 1 or claim 2 with a composition suspected of being acidic or basic and detecting the fluorescence of said compound as an indicator of said acidic or basic conditions.

5. The method according to claim 4 wherein said composition comprises an intracellular environment.

6. A compound selected from the group consisting of:
   i) 2-{(1E,3E,5E)-5-[3-(5-carboxypentyl)-3-methyl-5-sulfo-1,3-dihydro-2H-indol-2-ylidene]penta-1,3-dienyl}-3,3-dimethyl-5-sulfo-1-(4-sulfobutyl)-3H-indolium;
   ii) 3-(5-carboxypentyl)-2-[(1E,3E,5E)-5-(5,7-dichloro-3,3-dimethyl-1,3-dihydro -2H-indol-2-ylidene)penta-1,3-dienyl]-3-methyl-5-sulfo-1-(4-sulfobutyl)-3H-indolium;
   iii) 2-{(1E,3E,5E)-5-[3-(5-carboxypentyl)-3-methyl-5-sulfo-1,3-dihydro-2H-indol-2-ylidene]penta-1,3-dienyl}-5-chloro-3,3-dimethyl-1-(4-sulfobutyl)-3H-indolium;
   iv) 3-(5-carboxypentyl)-2-[(1E,3E,5E)-5-(7-chloro-3,3-dimethyl-5-sulfo- 1,3-dihydro-2H-indol-2-ylidene) penta-1,3-dienyl]-3-methyl-5-sulfo-1 -(4-sulfobutyl)-3H -indolium; and
   v) 3-(5-carboxypentyl)-3-methyl-2-{(1E,3E,5E)-5-[3-methyl-5-sulfo-3-(4-sulfobutyl)-1,3-dihydro-2H-indol-2-ylidene]penta-1,3-dienyl}-5-sulfo-1-(4-sulfobutyl)-3H -indolium.

7. A method for labelling and detecting a component of an aqueous liquid comprising:
   a) adding to said liquid containing said component a compound of claim 1 or claim 2 which compound is reactive with said component;
   b) reacting said compound with said component so that said compound becomes bound to and thereby labels said component; and
   c) detecting said labeled component by an optical method.

8. The method of claim 7 wherein said component is selected from any one of an antibody, protein, peptide, enzyme substrate, hormone, lymphokine, metabolite, receptor, antigen, hapten, lectin, avidin, streptavidin, toxin, carbohydrate, oligosaccharide, polysaccharide, nucleic acid, derivatized deoxy nucleic acid, DNA fragment, RNA fragment, derivatized DNA fragment, derivatized RNA fragment, nucleoside, nucleotide, natural drug, synthetic drug, virus particle, bacterial particle, virus component, yeast component, blood cell, blood cell component, plasma component, serum component, biological cell, noncellular blood component, bacteria, bacterial component, natural or synthetic lipid vesicle, poison, environmental pollutant, polymer, polymer particle, glass particle, glass surface, plastic particle, plastic surface, polymer membrane, conductor or semiconductor.

9. A compound of claim 3 wherein Q and W are independently selected from the group consisting of I, Br and Cl.

* * * * *